United States Patent
Gibson et al.

(10) Patent No.: US 12,131,828 B2
(45) Date of Patent: Oct. 29, 2024

(54) DEVICES, SYSTEMS, AND METHODS FOR ASSESSING FACILITY COMPLIANCE WITH INFECTIOUS DISEASE GUIDANCE

(71) Applicant: Honeywell International Inc., Charlotte, NC (US)

(72) Inventors: Adam Robert Gibson, Brunswick (AU); Rajkumar Palanivel, Eden Prairie, MN (US); Prabhat Ranjan, Bangalore (IN); Kelvin Paul Towler, Barnham (GB); Kendall Paix, Cherrybrook (AU); Mayur Sidram Salgar, Bangalore (IN); Sheeladitya Karmakar, Bangalore (IN); Manish Sharma, Alpharetta, GA (US)

(73) Assignee: HONEYWELL INTERNATIONA INC., Charlotte, NC (US)

( * ) Notice: Subject to any disclaimer, the term of this patent is extended or adjusted under 35 U.S.C. 154(b) by 781 days.

(21) Appl. No.: 17/314,565

(22) Filed: May 7, 2021

(65) Prior Publication Data
US 2021/0398690 A1    Dec. 23, 2021

Related U.S. Application Data

(60) Provisional application No. 63/042,389, filed on Jun. 22, 2020.

(51) Int. Cl.
*G16H 50/30* (2018.01)
*G16H 20/00* (2018.01)
*G16H 50/80* (2018.01)

(52) U.S. Cl.
CPC ............ *G16H 50/80* (2018.01); *G16H 20/00* (2018.01); *G16H 50/30* (2018.01)

(58) Field of Classification Search
CPC .......... G16H 50/80; G16H 50/30; G16G 20/00
See application file for complete search history.

(56) References Cited

U.S. PATENT DOCUMENTS

| 191,512 A | 6/1877 | Bennett et al. |
| 4,009,647 A | 3/1977 | Howorth |
| (Continued) | | |

FOREIGN PATENT DOCUMENTS

| CA | 2387100 A1 | 11/2003 |
| CA | 2538139 A1 | 3/2005 |
| (Continued) | | |

OTHER PUBLICATIONS

Johnson Controls Develops Industry-first AI Driven Digital Solution to Manage Clean Air, Energy, Sustainability, Comfort and Cost in Buildings, 7 pages, 2022. Accessed Aug. 29, 2022.

(Continued)

*Primary Examiner* — Gary Collins
(74) *Attorney, Agent, or Firm* — Seager, Tufte & Wickhem, LLP

(57) ABSTRACT

Devices, methods, and systems for monitoring and/or assessing compliance with infectious disease guidance for reducing infectious disease transmissions are described herein. The systems may include sensing devices at or within a facility and computing devices to compare data based on outputs from the sensing devices with guidance and/or recommendations for mitigating infectious disease transmission. Various compliance parameters may be identified as being relevant to the guidelines and measurable with outputs from the sensing devices. Various compliance parameters may be identified as being relevant to the guidelines, but not measurable with outputs from the sensing devices. The compliance parameters may be individually scored or scored in groups, including the compliance parameters not measureable with outputs from the sensing devices, (Continued)

and a score relative to a facility or group of facilities may be provided. The scores may be presented to via a dashboard.

19 Claims, 6 Drawing Sheets

(56) References Cited

U.S. PATENT DOCUMENTS

| | | |
|---|---|---|
| 4,375,637 A | 3/1983 | Desjardins |
| 4,918,615 A | 4/1990 | Suzuki et al. |
| 4,939,922 A | 7/1990 | Smalley et al. |
| 5,566,084 A | 10/1996 | Cmar |
| 5,727,579 A | 3/1998 | Chardack |
| 5,745,126 A | 4/1998 | Jain et al. |
| 5,751,916 A | 5/1998 | Kon et al. |
| 5,777,598 A | 7/1998 | Gowda et al. |
| 5,973,662 A | 10/1999 | Singers et al. |
| 6,065,842 A | 5/2000 | Fink |
| 6,139,177 A | 10/2000 | Venkatraman et al. |
| 6,144,993 A | 11/2000 | Fukunaga et al. |
| 6,157,943 A | 12/2000 | Meyer |
| 6,229,429 B1 | 5/2001 | Horon |
| 6,238,337 B1 | 5/2001 | Kambhatla et al. |
| 6,334,211 B1 | 12/2001 | Kojima et al. |
| 6,353,853 B1 | 3/2002 | Gravlin |
| 6,369,695 B2 | 4/2002 | Horon |
| 6,375,038 B1 | 4/2002 | Daansen et al. |
| 6,429,868 B1 | 8/2002 | Dehner, Jr. et al. |
| 6,473,084 B1 | 10/2002 | Phillips et al. |
| 6,487,457 B1 | 11/2002 | Hull et al. |
| 6,580,950 B1 | 6/2003 | Johnson et al. |
| 6,598,056 B1 | 7/2003 | Hull et al. |
| 6,619,555 B2 | 9/2003 | Rosen |
| 6,704,012 B1 | 3/2004 | Lefave |
| 6,720,874 B2 | 4/2004 | Fufido et al. |
| 6,741,915 B2 | 5/2004 | Poth |
| 6,796,896 B2 | 9/2004 | Laiti |
| 6,801,199 B1 | 10/2004 | Wallman |
| 6,816,878 B1 | 11/2004 | Zimmers et al. |
| 6,876,951 B2 | 4/2005 | Skidmore et al. |
| 6,882,278 B2 | 4/2005 | Winings et al. |
| 6,904,385 B1 | 6/2005 | Budike, Jr. |
| 6,907,387 B1 | 6/2005 | Reardon |
| 6,911,177 B2 | 6/2005 | Deal |
| 6,993,403 B1 | 1/2006 | Dadebo et al. |
| 6,993,417 B2 | 1/2006 | Osann, Jr. |
| 7,023,440 B1 | 4/2006 | Havekost et al. |
| 7,031,880 B1 | 4/2006 | Seem et al. |
| 7,062,722 B1 | 6/2006 | Carlin et al. |
| 7,110,843 B2 | 9/2006 | Pagnano et al. |
| 7,139,685 B2 | 11/2006 | Bascle et al. |
| 7,164,972 B2 | 1/2007 | Imhof et al. |
| 7,183,899 B2 | 2/2007 | Behnke |
| 7,200,639 B1 | 4/2007 | Yoshida |
| 7,222,111 B1 | 5/2007 | Budike, Jr. |
| 7,222,800 B2 | 5/2007 | Wruck |
| 7,257,397 B2 | 8/2007 | Shamoon et al. |
| 7,280,030 B1 | 10/2007 | Monaco |
| 7,292,908 B2 | 11/2007 | Borne et al. |
| 7,295,116 B2 | 11/2007 | Kumar et al. |
| 7,302,313 B2 | 11/2007 | Sharp et al. |
| 7,308,323 B2 | 12/2007 | Kruk et al. |
| 7,308,388 B2 | 12/2007 | Beverina et al. |
| 7,313,447 B2 | 12/2007 | Hsiung et al. |
| 7,346,433 B2 | 3/2008 | Budike, Jr. |
| 7,356,548 B1 | 4/2008 | Culp et al. |
| 7,379,782 B1 | 5/2008 | Cocco |
| 7,383,148 B2 | 6/2008 | Ahmed |
| 7,434,742 B2 | 10/2008 | Mueller et al. |
| 7,447,333 B1 | 11/2008 | Masticola et al. |
| 7,466,224 B2 | 12/2008 | Ward et al. |
| 7,496,472 B2 | 2/2009 | Seem |
| 7,512,450 B2 | 3/2009 | Ahmed |
| 7,516,490 B2 | 4/2009 | Riordan et al. |
| 7,548,833 B2 | 6/2009 | Ahmed |
| 7,551,092 B1 | 6/2009 | Henry |
| 7,557,729 B2 | 7/2009 | Hubbard et al. |
| 7,567,844 B2 | 7/2009 | Thomas et al. |
| 7,596,473 B2 | 9/2009 | Hansen et al. |
| 7,610,910 B2 | 11/2009 | Ahmed |
| 7,626,507 B2 | 12/2009 | LaCasse |
| 7,664,574 B2 | 2/2010 | Imhof et al. |
| 7,682,464 B2 | 3/2010 | Glenn et al. |
| 7,688,212 B2 | 3/2010 | Farley |
| 7,702,421 B2 | 4/2010 | Sullivan et al. |
| 7,729,882 B2 | 6/2010 | Seem |
| 7,755,494 B2 | 7/2010 | Melker et al. |
| 7,761,310 B2 | 7/2010 | Rodgers |
| 7,774,227 B2 | 8/2010 | Srivastava |
| 7,797,188 B2 | 9/2010 | Srivastava |
| 7,819,136 B1 | 10/2010 | Eddy |
| 7,822,806 B2 | 10/2010 | Frank et al. |
| 7,856,370 B2 | 12/2010 | Katta et al. |
| 7,978,083 B2 | 7/2011 | Melker et al. |
| 7,984,384 B2 | 7/2011 | Chaudhri et al. |
| 7,986,323 B2 | 7/2011 | Kobayashi et al. |
| 8,024,666 B2 | 9/2011 | Thompson |
| 8,086,047 B2 | 12/2011 | Penke et al. |
| 8,099,178 B2 | 1/2012 | Mairs et al. |
| 8,151,280 B2 | 4/2012 | Sather et al. |
| 8,176,095 B2 | 5/2012 | Murray et al. |
| 8,218,871 B2 | 7/2012 | Angell et al. |
| 8,219,660 B2 | 7/2012 | McCoy et al. |
| 8,271,941 B2 | 9/2012 | Zhang et al. |
| 8,294,585 B2 | 10/2012 | Barnhill |
| 8,302,020 B2 | 10/2012 | Louch et al. |
| 8,320,634 B2 | 11/2012 | Deutsch |
| 8,334,422 B2 | 12/2012 | Gutsol et al. |
| 8,344,893 B1 | 1/2013 | Drammeh |
| 8,375,118 B2 | 2/2013 | Hao et al. |
| 8,473,080 B2 | 6/2013 | Seem et al. |
| 8,476,590 B2 | 7/2013 | Stratmann et al. |
| 8,516,016 B2 | 8/2013 | Park et al. |
| 8,558,660 B2 | 10/2013 | Nix et al. |
| 8,639,527 B2 | 1/2014 | Rensvold et al. |
| 8,698,637 B2 | 4/2014 | Raichman |
| 8,816,860 B2 | 8/2014 | Ophardt et al. |
| 8,869,027 B2 | 10/2014 | Louch et al. |
| 8,904,497 B2 | 12/2014 | Hsieh |
| 8,936,944 B2 | 1/2015 | Peltz et al. |
| 8,947,437 B2 | 2/2015 | Garr et al. |
| 8,950,019 B2 | 2/2015 | Loberger et al. |
| 9,000,926 B2 | 4/2015 | Hollock et al. |
| 9,002,532 B2 | 4/2015 | Asmus |
| 9,030,325 B2 | 5/2015 | Taneff |
| 9,098,738 B2 | 8/2015 | Bilet et al. |
| 9,105,071 B2 | 8/2015 | Fletcher et al. |
| 9,175,356 B2 | 11/2015 | Peltz et al. |
| 9,235,657 B1 | 1/2016 | Wenzel et al. |
| 9,240,111 B2 | 1/2016 | Scott et al. |
| 9,256,702 B2 | 2/2016 | Elbsat et al. |
| 9,280,884 B1 | 3/2016 | Schultz et al. |
| 9,292,972 B2 | 3/2016 | Hailemariam et al. |
| 9,320,662 B2 | 4/2016 | Hayes et al. |
| 9,322,566 B2 | 4/2016 | Wenzel et al. |
| 9,355,069 B2 | 5/2016 | Elbsat et al. |
| 9,370,600 B1 | 6/2016 | DuPuis et al. |
| 9,373,242 B1 | 6/2016 | Conrad et al. |
| 9,396,638 B2 | 7/2016 | Wildman et al. |
| 9,311,807 B2 | 8/2016 | Schultz et al. |
| 9,406,212 B2 | 8/2016 | De Luca et al. |
| 9,418,535 B1 | 8/2016 | Felch et al. |
| 9,418,536 B1 | 8/2016 | Felch et al. |
| 9,436,179 B1 | 9/2016 | Turney et al. |
| 9,449,219 B2 | 9/2016 | Bilet et al. |
| 9,477,543 B2 | 10/2016 | Henley et al. |
| 9,497,832 B2 | 11/2016 | Verberkt et al. |
| 9,513,364 B2 | 12/2016 | Hall et al. |
| 9,526,380 B2 | 12/2016 | Hamilton et al. |
| 9,526,806 B2 | 12/2016 | Park et al. |
| 9,536,415 B2 | 1/2017 | De Luca et al. |
| 9,558,648 B2 | 1/2017 | Douglas |
| 9,568,204 B2 | 2/2017 | Asmus et al. |
| 9,581,985 B2 | 2/2017 | Walser et al. |

(56) References Cited

U.S. PATENT DOCUMENTS

| | | | |
|---|---|---|---|
| 9,591,267 B2 | 3/2017 | Lipton et al. |
| 9,606,520 B2 | 3/2017 | Noboa et al. |
| 9,612,601 B2 | 4/2017 | Beyhaghi et al. |
| 9,613,518 B2 | 4/2017 | Dunn et al. |
| 9,618,224 B2 | 4/2017 | Emmons et al. |
| 9,640,059 B2 | 5/2017 | Hyland |
| 9,672,360 B2 | 6/2017 | Barkan |
| 9,696,054 B2 | 7/2017 | Asmus |
| 9,710,700 B2 | 7/2017 | Bilet et al. |
| 9,715,242 B2 | 7/2017 | Pillai et al. |
| 9,721,452 B2 | 8/2017 | Felch et al. |
| 9,729,945 B2 | 8/2017 | Schultz et al. |
| 9,778,639 B2 | 10/2017 | Boettcher et al. |
| 9,784,464 B2 | 10/2017 | Yamamoto et al. |
| 9,798,336 B2 | 10/2017 | Przybylski |
| 9,843,743 B2 | 12/2017 | Lewis et al. |
| 9,852,481 B1 | 12/2017 | Turney et al. |
| 9,856,634 B2 | 1/2018 | Rodenbeck et al. |
| 9,872,088 B2 | 1/2018 | Fadell et al. |
| 9,875,639 B2 | 1/2018 | Bone et al. |
| 9,911,312 B2 | 3/2018 | Wildman et al. |
| 9,940,819 B2 | 4/2018 | Ferniany |
| 9,956,306 B2 | 5/2018 | Brais et al. |
| 9,982,903 B1 | 5/2018 | Ridder et al. |
| 9,986,175 B2 | 5/2018 | Frank et al. |
| 10,007,259 B2 | 6/2018 | Turney et al. |
| 10,055,114 B2 | 8/2018 | Shah et al. |
| 10,087,608 B2 | 10/2018 | Dobizl et al. |
| 10,101,730 B2 | 10/2018 | Wenzel et al. |
| 10,101,731 B2 | 10/2018 | Asmus et al. |
| 10,175,681 B2 | 1/2019 | Wenzel et al. |
| 10,222,083 B2 | 3/2019 | Drees et al. |
| 10,223,894 B2 | 3/2019 | Raichman |
| 10,228,837 B2 | 3/2019 | Hua et al. |
| 10,235,865 B2 | 3/2019 | Thyroff |
| 10,251,610 B2 | 4/2019 | Parthasarathy et al. |
| 10,282,796 B2 | 5/2019 | Elbsat et al. |
| 10,288,306 B2 | 5/2019 | Ridder et al. |
| 10,303,843 B2 | 5/2019 | Bitran et al. |
| 10,317,864 B2 | 6/2019 | Boettcher et al. |
| 10,332,382 B2 | 6/2019 | Thyroff |
| 10,359,748 B2 | 7/2019 | Elbsat et al. |
| 10,386,820 B2 | 8/2019 | Wenzel et al. |
| 10,402,767 B2 | 9/2019 | Noboa et al. |
| 10,514,178 B2 | 12/2019 | Willmott et al. |
| 10,514,817 B2 | 12/2019 | Hua et al. |
| 10,520,210 B2 | 12/2019 | Park et al. |
| 10,544,955 B2 | 1/2020 | Przybylski |
| 10,558,178 B2 | 2/2020 | Willmott et al. |
| 10,559,180 B2 | 2/2020 | Pourmohammad et al. |
| 10,559,181 B2 | 2/2020 | Pourmohammad et al. |
| 10,565,844 B2 | 2/2020 | Pourmohammad et al. |
| 10,600,263 B2 | 3/2020 | Park et al. |
| 10,602,474 B2 | 3/2020 | Goldstein |
| 10,605,477 B2 | 3/2020 | Ridder |
| 10,607,147 B2 | 3/2020 | Raykov et al. |
| 10,619,882 B2 | 4/2020 | Chatterjee et al. |
| 10,627,124 B2 | 4/2020 | Walser et al. |
| 10,673,380 B2 | 6/2020 | Wenzel et al. |
| 10,678,227 B2 | 6/2020 | Przybylski et al. |
| 10,706,375 B2 | 7/2020 | Wenzel et al. |
| 10,726,711 B2 | 7/2020 | Subramanian et al. |
| 10,732,584 B2 | 8/2020 | Elbsat et al. |
| 10,767,885 B2 | 9/2020 | Przybylski et al. |
| 10,775,988 B2 | 9/2020 | Narain et al. |
| 10,796,554 B2 | 10/2020 | Vincent et al. |
| 10,809,682 B2 | 10/2020 | Patil et al. |
| 10,809,705 B2 | 10/2020 | Przybylski |
| 10,824,125 B2 | 11/2020 | Elbsat et al. |
| 10,854,194 B2 | 12/2020 | Park et al. |
| 10,871,298 B2 | 12/2020 | Ridder et al. |
| 10,876,754 B2 | 12/2020 | Wenzel et al. |
| 10,890,904 B2 | 1/2021 | Turney et al. |
| 10,900,686 B2 | 1/2021 | Willmott et al. |
| 10,901,446 B2 | 1/2021 | Nesler et al. |
| 10,909,642 B2 | 2/2021 | Elbsat et al. |
| 10,915,094 B2 | 2/2021 | Wenzel et al. |
| 10,917,740 B1 | 2/2021 | Scott et al. |
| 10,921,972 B2 | 2/2021 | Park et al. |
| 10,921,973 B2 | 2/2021 | Park et al. |
| 10,928,790 B2 | 2/2021 | Mueller et al. |
| 10,948,884 B2 | 3/2021 | Beaty et al. |
| 10,949,777 B2 | 3/2021 | Elbsat et al. |
| 10,955,800 B2 | 3/2021 | Burroughs et al. |
| 10,956,842 B2 | 3/2021 | Wenzel et al. |
| 10,962,945 B2 | 3/2021 | Park et al. |
| 10,969,135 B2 | 4/2021 | Willmott et al. |
| 11,002,457 B2 | 5/2021 | Turney et al. |
| 11,009,252 B2 | 5/2021 | Turney et al. |
| 11,010,846 B2 | 5/2021 | Elbsat et al. |
| 11,016,648 B2 | 5/2021 | Fala et al. |
| 11,016,998 B2 | 5/2021 | Park et al. |
| 11,022,947 B2 | 6/2021 | Elbsat et al. |
| 11,024,292 B2 | 6/2021 | Park et al. |
| 11,036,249 B2 | 6/2021 | Elbsat |
| 11,038,709 B2 | 6/2021 | Park et al. |
| 11,042,139 B2 | 6/2021 | Deshpande et al. |
| 11,042,924 B2 | 6/2021 | Asmus et al. |
| 11,061,424 B2 | 7/2021 | Elbsat et al. |
| 11,068,821 B2 | 7/2021 | Wenzel et al. |
| 11,070,389 B2 | 7/2021 | Schuster et al. |
| 11,073,976 B2 | 7/2021 | Park et al. |
| 11,080,289 B2 | 8/2021 | Park et al. |
| 11,080,426 B2 | 8/2021 | Park et al. |
| 11,086,276 B2 | 8/2021 | Wenzel et al. |
| 11,094,186 B2 | 8/2021 | Razak |
| 11,108,587 B2 | 8/2021 | Park et al. |
| 11,131,473 B2 | 8/2021 | Risbeck et al. |
| 11,113,295 B2 | 9/2021 | Park et al. |
| 11,119,458 B2 | 9/2021 | Asp et al. |
| 11,120,012 B2 | 9/2021 | Park et al. |
| 11,150,617 B2 | 10/2021 | Ploegert et al. |
| 11,151,983 B2 | 10/2021 | Park et al. |
| 11,156,996 B2 | 10/2021 | Schuster et al. |
| 11,158,306 B2 | 10/2021 | Park et al. |
| 11,182,047 B2 | 11/2021 | Nayak et al. |
| 11,195,401 B2 | 12/2021 | Pourmohammad |
| 11,217,087 B2 | 1/2022 | Pelski |
| 11,226,126 B2 | 1/2022 | Przybylski et al. |
| 11,243,523 B2 | 2/2022 | Llopis et al. |
| 11,268,715 B2 | 3/2022 | Park et al. |
| 11,268,996 B2 | 3/2022 | Vitullo et al. |
| 11,269,505 B2 | 3/2022 | Fala et al. |
| 11,272,011 B1 | 3/2022 | Laughton et al. |
| 11,272,316 B2 | 3/2022 | Scott et al. |
| 11,275,348 B2 | 3/2022 | Park et al. |
| 11,275,363 B2 | 3/2022 | Przybylski et al. |
| 11,281,169 B2 | 3/2022 | Chatterjee et al. |
| 11,288,754 B2 | 3/2022 | Elbsat et al. |
| 11,314,726 B2 | 4/2022 | Park et al. |
| 11,314,788 B2 | 4/2022 | Park et al. |
| 11,334,044 B2 | 5/2022 | Goyal |
| 11,353,834 B2 | 6/2022 | Mueller et al. |
| 11,356,292 B2 | 6/2022 | Ploegert et al. |
| 11,360,451 B2 | 6/2022 | Pancholi et al. |
| 11,361,123 B2 | 6/2022 | Ploegert et al. |
| 11,888,093 B2 | 1/2024 | Zhang et al. |
| 2002/0111698 A1 | 8/2002 | Graziano et al. |
| 2002/0130868 A1 | 9/2002 | Smith |
| 2003/0028269 A1 | 2/2003 | Spriggs et al. |
| 2003/0030637 A1 | 2/2003 | Grinstein et al. |
| 2003/0046862 A1 | 3/2003 | Wolf et al. |
| 2003/0071814 A1 | 4/2003 | Jou et al. |
| 2003/0078677 A1 | 4/2003 | Hull et al. |
| 2003/0083957 A1 | 5/2003 | Olefson |
| 2003/0103075 A1 | 6/2003 | Rosselot |
| 2003/0171851 A1 | 9/2003 | Brickfield et al. |
| 2003/0214400 A1 | 11/2003 | Mizutani et al. |
| 2003/0233432 A1 | 12/2003 | Davis et al. |
| 2004/0001009 A1 | 1/2004 | Winings et al. |
| 2004/0064260 A1 | 4/2004 | Padmanabhan et al. |
| 2004/0143474 A1 | 7/2004 | Haeberle et al. |
| 2004/0153437 A1 | 8/2004 | Buchan |
| 2004/0168115 A1 | 8/2004 | Bauernschmidt et al. |

(56) References Cited

U.S. PATENT DOCUMENTS

| | | |
|---|---|---|
| 2004/0233192 A1 | 11/2004 | Hopper |
| 2004/0260411 A1 | 12/2004 | Cannon |
| 2005/0010460 A1 | 1/2005 | Mizoguchi et al. |
| 2005/0119767 A1 | 6/2005 | Kiwimagi et al. |
| 2005/0143863 A1 | 6/2005 | Ruane et al. |
| 2005/0267900 A1 | 12/2005 | Ahmed et al. |
| 2006/0004841 A1 | 1/2006 | Heikkonen et al. |
| 2006/0009862 A1 | 1/2006 | Imhof et al. |
| 2006/0017547 A1 | 1/2006 | Buckingham et al. |
| 2006/0020177 A1 | 1/2006 | Seo et al. |
| 2006/0028471 A1 | 2/2006 | Kincaid et al. |
| 2006/0029256 A1 | 2/2006 | Miyoshi et al. |
| 2006/0058900 A1 | 3/2006 | Johanson et al. |
| 2006/0067545 A1 | 3/2006 | Lewis et al. |
| 2006/0067546 A1 | 3/2006 | Lewis et al. |
| 2006/0077255 A1 | 4/2006 | Cheng |
| 2006/0184326 A1 | 8/2006 | McNally et al. |
| 2006/0231568 A1 | 10/2006 | Lynn et al. |
| 2006/0265664 A1 | 11/2006 | Simons et al. |
| 2006/0279630 A1 | 12/2006 | Aggarwal et al. |
| 2007/0016955 A1 | 1/2007 | Goldberg et al. |
| 2007/0055757 A1 | 3/2007 | Mairs et al. |
| 2007/0055760 A1 | 3/2007 | McCoy et al. |
| 2007/0061046 A1 | 3/2007 | Mairs et al. |
| 2007/0067062 A1 | 3/2007 | Mairs et al. |
| 2007/0088534 A1 | 4/2007 | MacArthur et al. |
| 2007/0090951 A1 | 4/2007 | Chan et al. |
| 2007/0091091 A1 | 4/2007 | Gardiner et al. |
| 2007/0101433 A1 | 5/2007 | Louch et al. |
| 2007/0114295 A1 | 5/2007 | Jenkins |
| 2007/0120652 A1 | 5/2007 | Behnke |
| 2007/0139208 A1 | 6/2007 | Kates |
| 2007/0216682 A1 | 9/2007 | Navratil et al. |
| 2007/0219645 A1 | 9/2007 | Thomas et al. |
| 2007/0239484 A1 | 10/2007 | Arond et al. |
| 2007/0268122 A1 | 11/2007 | Kow et al. |
| 2008/0001763 A1 | 1/2008 | Raja et al. |
| 2008/0027885 A1 | 1/2008 | Van Putten et al. |
| 2008/0036593 A1 | 2/2008 | Rose-Pehrsson et al. |
| 2008/0062167 A1 | 3/2008 | Boggs et al. |
| 2008/0099045 A1 | 5/2008 | Glenn et al. |
| 2008/0103798 A1 | 5/2008 | Domenikos et al. |
| 2008/0120396 A1 | 5/2008 | Jayaram et al. |
| 2008/0144885 A1 | 6/2008 | Zucherman et al. |
| 2008/0183424 A1 | 7/2008 | Seem |
| 2008/0194009 A1 | 8/2008 | Marentis |
| 2008/0198231 A1 | 8/2008 | Ozdemir et al. |
| 2008/0209342 A1 | 8/2008 | Taylor et al. |
| 2008/0222565 A1 | 9/2008 | Taylor et al. |
| 2008/0224862 A1 | 9/2008 | Cirker |
| 2008/0242945 A1 | 10/2008 | Gugliotti et al. |
| 2008/0250800 A1 | 10/2008 | Wetzel |
| 2008/0279420 A1 | 11/2008 | Masticola et al. |
| 2008/0280275 A1 | 11/2008 | Collopy |
| 2008/0303658 A1 | 12/2008 | Melker et al. |
| 2008/0306985 A1 | 12/2008 | Murray et al. |
| 2008/0320552 A1 | 12/2008 | Kumar et al. |
| 2009/0001181 A1 | 1/2009 | Siddaramanna et al. |
| 2009/0024944 A1 | 1/2009 | Louch et al. |
| 2009/0065596 A1 | 3/2009 | Seem et al. |
| 2009/0083120 A1 | 3/2009 | Strichman et al. |
| 2009/0096791 A1 | 4/2009 | Abshear et al. |
| 2009/0125337 A1 | 5/2009 | Abri |
| 2009/0125825 A1 | 5/2009 | Rye et al. |
| 2009/0144023 A1 | 6/2009 | Seem |
| 2009/0157744 A1 | 6/2009 | McConnell |
| 2009/0160673 A1 | 6/2009 | Cirker |
| 2009/0322782 A1 | 12/2009 | Kimchi et al. |
| 2010/0048167 A1 | 2/2010 | Chow et al. |
| 2010/0058248 A1 | 3/2010 | Park |
| 2010/0064001 A1 | 3/2010 | Daily |
| 2010/0070089 A1 | 3/2010 | Harrod et al. |
| 2010/0073162 A1 | 3/2010 | Johnson et al. |
| 2010/0123560 A1 | 5/2010 | Nix et al. |
| 2010/0134296 A1 | 6/2010 | Hwang |
| 2010/0156628 A1 | 6/2010 | Ainsbury et al. |
| 2010/0156630 A1 | 6/2010 | Ainsbury |
| 2010/0188228 A1 | 7/2010 | Hyland |
| 2010/0223198 A1 | 9/2010 | Noureldin et al. |
| 2010/0249955 A1 | 9/2010 | Sitton |
| 2010/0286937 A1 | 11/2010 | Hedley et al. |
| 2010/0318200 A1 | 12/2010 | Foslien et al. |
| 2010/0324962 A1 | 12/2010 | Nesler et al. |
| 2011/0010654 A1 | 1/2011 | Raymond et al. |
| 2011/0057799 A1 | 3/2011 | Taneff |
| 2011/0077779 A1 | 3/2011 | Fuller et al. |
| 2011/0083094 A1 | 4/2011 | Laycock et al. |
| 2011/0087988 A1 | 4/2011 | Ray et al. |
| 2011/0112854 A1 | 5/2011 | Koch et al. |
| 2011/0126111 A1 | 5/2011 | Gill et al. |
| 2011/0154426 A1 | 6/2011 | Doser et al. |
| 2011/0161124 A1 | 6/2011 | Lappinga et al. |
| 2011/0169646 A1 | 7/2011 | Raichman |
| 2011/0184563 A1 | 7/2011 | Foslien et al. |
| 2011/0202467 A1 | 8/2011 | Hilber et al. |
| 2011/0273298 A1 | 11/2011 | Snodgrass et al. |
| 2011/0291841 A1 | 12/2011 | Hollock et al. |
| 2011/0298301 A1 | 12/2011 | Wong et al. |
| 2011/0316703 A1 | 12/2011 | Butler et al. |
| 2011/0320054 A1 | 12/2011 | Brzezowski |
| 2012/0022700 A1 | 1/2012 | Drees et al. |
| 2012/0039503 A1 | 2/2012 | Chen et al. |
| 2012/0062382 A1 | 3/2012 | Taneff |
| 2012/0075464 A1 | 3/2012 | Derenne et al. |
| 2012/0109988 A1 | 5/2012 | Li et al. |
| 2012/0112883 A1 | 5/2012 | Wallace et al. |
| 2012/0131217 A1 | 5/2012 | Delorme et al. |
| 2012/0158185 A1 | 6/2012 | El-Mankabady et al. |
| 2012/0216243 A1 | 8/2012 | Gill et al. |
| 2012/0224057 A1 | 9/2012 | Gill et al. |
| 2012/0259466 A1 | 10/2012 | Ray et al. |
| 2012/0262472 A1 | 10/2012 | Garr et al. |
| 2012/0272146 A1 | 10/2012 | D'souza et al. |
| 2012/0291068 A1 | 11/2012 | Khushoo et al. |
| 2012/0303652 A1 | 11/2012 | Tseng |
| 2012/0310418 A1 | 12/2012 | Harrod et al. |
| 2013/0055132 A1 | 2/2013 | Foslien |
| 2013/0060794 A1 | 3/2013 | Puttabasappa et al. |
| 2013/0082842 A1 | 4/2013 | Balazs et al. |
| 2013/0086152 A1 | 4/2013 | Hersche et al. |
| 2013/0091631 A1 | 4/2013 | Hayes et al. |
| 2013/0110295 A1 | 5/2013 | Zheng et al. |
| 2013/0169681 A1 | 7/2013 | Rasane et al. |
| 2013/0184880 A1 | 7/2013 | McMahon |
| 2013/0187775 A1 | 7/2013 | Marsden et al. |
| 2013/0204570 A1 | 8/2013 | Mendelson et al. |
| 2013/0229276 A1 | 9/2013 | Hunter |
| 2013/0268293 A1 | 10/2013 | Knudson et al. |
| 2013/0289774 A1 | 10/2013 | Day et al. |
| 2013/0338837 A1 | 12/2013 | Hublou et al. |
| 2014/0032157 A1 | 1/2014 | Khiani |
| 2014/0040998 A1 | 2/2014 | Hsieh |
| 2014/0046490 A1 | 2/2014 | Foslien et al. |
| 2014/0046722 A1 | 2/2014 | Rosenbloom et al. |
| 2014/0058539 A1 | 2/2014 | Park |
| 2014/0167917 A2 | 6/2014 | Wallace et al. |
| 2014/0207291 A1 | 7/2014 | Golden et al. |
| 2014/0292518 A1 | 10/2014 | Wildman et al. |
| 2014/0307076 A1 | 10/2014 | Deutsch |
| 2014/0309757 A1 | 10/2014 | Le Sant et al. |
| 2014/0316582 A1 | 10/2014 | Berg-Sonne et al. |
| 2014/0320289 A1 | 10/2014 | Raichman |
| 2014/0342724 A1 | 11/2014 | Hill et al. |
| 2015/0025329 A1 | 1/2015 | Amarasingham et al. |
| 2015/0032264 A1 | 1/2015 | Emmons et al. |
| 2015/0056909 A1 | 2/2015 | Chien |
| 2015/0070174 A1 | 3/2015 | Douglas |
| 2015/0077258 A1 | 3/2015 | Nelson et al. |
| 2015/0113462 A1 | 4/2015 | Chen et al. |
| 2015/0153918 A1 | 6/2015 | Chen et al. |
| 2015/0161874 A1 | 6/2015 | Thyroff et al. |
| 2015/0167995 A1 | 6/2015 | Fadell et al. |
| 2015/0168949 A1 | 6/2015 | Hua et al. |
| 2015/0194043 A1 | 7/2015 | Dunn et al. |

(56) References Cited

U.S. PATENT DOCUMENTS

| | | |
|---|---|---|
| 2015/0198707 A1 | 7/2015 | Al-Alusi |
| 2015/0212717 A1 | 7/2015 | Nair et al. |
| 2015/0213222 A1 | 7/2015 | Amarasingham et al. |
| 2015/0213379 A1 | 7/2015 | Nair et al. |
| 2015/0216369 A1 | 8/2015 | Hamilton et al. |
| 2015/0253748 A1 | 9/2015 | Brun et al. |
| 2015/0281287 A1 | 10/2015 | Gill et al. |
| 2015/0371347 A1* | 12/2015 | Hayward ............ G16H 10/20 705/314 |
| 2016/0061476 A1 | 3/2016 | Schultz et al. |
| 2016/0061477 A1 | 3/2016 | Schultz et al. |
| 2016/0061794 A1 | 3/2016 | Schultz et al. |
| 2016/0061795 A1 | 3/2016 | Schultz et al. |
| 2016/0063833 A1 | 3/2016 | Schultz et al. |
| 2016/0066067 A1 | 3/2016 | Schultz et al. |
| 2016/0116181 A1 | 4/2016 | Aultman et al. |
| 2016/0139067 A1 | 5/2016 | Grace |
| 2016/0253897 A1 | 9/2016 | Wildman et al. |
| 2016/0255516 A1 | 9/2016 | Hill et al. |
| 2016/0298864 A1 | 10/2016 | Ekolind et al. |
| 2016/0306934 A1 | 10/2016 | Sperry et al. |
| 2016/0314683 A1 | 10/2016 | Felch et al. |
| 2016/0328948 A1 | 11/2016 | Ferniany |
| 2016/0335731 A1 | 11/2016 | Hall |
| 2016/0367925 A1 | 12/2016 | Blackley |
| 2016/0379511 A1 | 12/2016 | Dawson et al. |
| 2017/0024986 A1 | 1/2017 | Austin |
| 2017/0193792 A1 | 7/2017 | Bermudez Rodriguez et al. |
| 2017/0256155 A1 | 9/2017 | Sengstaken, Jr. |
| 2017/0280949 A1 | 10/2017 | Wildman et al. |
| 2017/0294106 A1 | 10/2017 | Thyroff |
| 2017/0365024 A1 | 12/2017 | Koch et al. |
| 2018/0016773 A1 | 1/2018 | Chandler et al. |
| 2018/0151054 A1 | 5/2018 | Pi |
| 2018/0218591 A1 | 8/2018 | Easter |
| 2018/0259927 A1 | 9/2018 | Przybylski et al. |
| 2018/0293038 A1 | 10/2018 | Meruva et al. |
| 2018/0301014 A1 | 10/2018 | Worral et al. |
| 2018/0313695 A1 | 11/2018 | Shim et al. |
| 2018/0341760 A1* | 11/2018 | Frempong ............ H04W 12/63 |
| 2018/0365957 A1 | 12/2018 | Wright et al. |
| 2019/0051138 A1 | 2/2019 | Easter |
| 2019/0122759 A1 | 4/2019 | Wakimoto |
| 2019/0139395 A1 | 5/2019 | Rogachev et al. |
| 2019/0209719 A1 | 7/2019 | Andersen et al. |
| 2020/0009280 A1 | 1/2020 | Kupa et al. |
| 2020/0074836 A1 | 3/2020 | Kolavennu et al. |
| 2020/0090089 A1 | 3/2020 | Aston et al. |
| 2020/0106633 A1* | 4/2020 | Park ................... H04L 12/2827 |
| 2020/0146557 A1 | 5/2020 | Cheung et al. |
| 2020/0200420 A1 | 6/2020 | Nayak et al. |
| 2021/0010701 A1 | 1/2021 | Suindykov et al. |
| 2021/0011443 A1 | 1/2021 | Mcnamara et al. |
| 2021/0011444 A1 | 1/2021 | Risbeck et al. |
| 2021/0364181 A1 | 11/2021 | Risbeck et al. |
| 2021/0373519 A1 | 12/2021 | Risbeck et al. |
| 2022/0011731 A1 | 1/2022 | Risbeck et al. |
| 2022/0113045 A1 | 4/2022 | Gamroth et al. |
| 2022/0137580 A1 | 5/2022 | Burroughs et al. |

FOREIGN PATENT DOCUMENTS

| | | |
|---|---|---|
| CN | 103110410 A | 5/2013 |
| CN | 103970977 A | 8/2014 |
| CN | 105116848 A | 12/2015 |
| CN | 108961714 A | 12/2018 |
| CN | 110009245 A | 7/2019 |
| CN | 110084928 A | 8/2019 |
| CN | 110827457 A | 2/2020 |
| EP | 1669912 A1 | 6/2006 |
| EP | 2310981 A1 | 4/2011 |
| EP | 3680914 A1 | 7/2020 |
| JP | 7085166 A | 3/1995 |
| JP | 11024735 A | 1/1999 |
| JP | 11317936 A | 11/1999 |
| JP | 2001356813 A | 12/2001 |
| JP | 2005242531 A | 9/2005 |
| JP | 2005311563 A | 11/2005 |
| KR | 1172747 B1 | 8/2012 |
| KR | 101445367 B1 | 10/2014 |
| KR | 1499081 B1 | 3/2015 |
| WO | 9621264 A3 | 11/1996 |
| WO | 2004029518 A1 | 4/2004 |
| WO | 2005045715 A2 | 5/2005 |
| WO | 2008152433 A1 | 12/2008 |
| WO | 2008157755 A1 | 12/2008 |
| WO | 2009012319 A2 | 1/2009 |
| WO | 2009079648 A1 | 6/2009 |
| WO | 2010106474 A1 | 9/2010 |
| WO | 2011025085 A1 | 3/2011 |
| WO | 2011043732 A1 | 4/2011 |
| WO | 2011057173 A2 | 5/2011 |
| WO | 2011123743 A1 | 10/2011 |
| WO | 2013062725 A1 | 5/2013 |
| WO | 2013178819 A1 | 12/2013 |
| WO | 2014009291 A1 | 1/2014 |
| WO | 2014098861 A1 | 6/2014 |
| WO | 2014135517 A1 | 9/2014 |
| WO | 2016123536 A1 | 8/2016 |
| WO | 2017057274 A1 | 4/2017 |
| WO | 2019046580 A1 | 3/2019 |
| WO | 2020024553 A1 | 2/2020 |

OTHER PUBLICATIONS

Johnson Controls and Microsoft Announce Global Collaboration, Launch Integration between Open Blue Digital Twin and Azure Digital Twins, 7 pages, 2022. Accessed Aug. 29, 2022.

Open Blue Companion Desktop User Guide, Johnson Controls, 18 pages, 2022.

Open Blue Digital Twin:Designed for Buildings. Infused with AI, Johnson Controls, 17 pages, 2022. Accessed Aug. 29, 2022.

Open Blue Enterprise Manager User Guide, Johnson Controls, Release 3.1, 72 pages, Jan. 28, 2021.

Open Blue Enterprise Manager User Guide, Johnson Controls, Release 4.0, 78pages, Nov. 29, 2021.

Open Blue Location Manager User Guide, Johnson Controls, Release 2.4.7, 28 pages, Jul. 20, 2022.

Open Blue Enterprise Manager, Optimize Building Portfolio Performance with Advanced Data Analytics and AI, Johnson Controls, 20 pages, Accessed Aug. 29, 2022.

Open Blue Platform, Make Smarter, Faster, More Data-Driven Decisions, Johnson Controls, 15 pages, 2022. Accessed Aug. 29, 2022.

Open Blue, Now, Spaces have Memory and Identity, Johnson Controls, 20 pages, 2022. Accessed Feb. 10, 2022.

Open Blue Enterprise Manager User Guide, Johnson Controls, 108 pages, Release 4.1.3, 2022, Accessed Aug. 29, 2022.

Risbeck et al; "Modeling and Multiobjective Optimization of Indoor Airborne Disease Transmission Risk and Associated Energy Consumption for Building HVAC Systems," Energy and Buildings, vol. 253, 24 pages, 2021.

Sinha et al; "Balance Infection Risk, Sustainability and Comfort with Open Blue," Johnson Controls, 2 pages, 2021.

Examiner's Report, CA Patent Office, CA Application No. 3, 120,445, Jan. 3, 2023 (5 pgs).

Bocicor et al. "Wireless Sensor Network based System for the Prevention of Hospital Acquired Infections", arxiv.org, Cornell University Ithaca, NY 14853, May 2, 2017, XP080947042, (Abstract).

Shhedi et al., "Traditional and ICT Solutions for Preventing the Hospital Acquired Infection", 2015 20th International Conference on Control Systems and Computer Science, IEEE, May 27, 2015, pp. 867-873, XP033188038.

Extended European Search Report, EP application No. 20151295.1, pp. 13, May 26, 2020.

U.S. Appl. No. 14/109,496, filed Dec. 17, 2013.

"What is the GE Nucleus Home Manager? How can a Home Manager Help with Energy Conservation?" GE Nucleus, 2 pages, printed Jan. 15, 2013. www.geappliances.com/home-energy-manager/about-energy-monitors.htm.

(56) References Cited

OTHER PUBLICATIONS

"Lucid Design Group—Building Dashboard Network—Apps," 7 pages, Jan. 15, 2013. www.luciddesigngroup.com/network/apps.php#homepage.
Preuveneers et al., "Intelligent Widgets for Intuitive Interaction and Coordination in Smart Home Environments," IEEE Eighth International Conference on Intelligent Environments, pp. 157-164, 2012.
Wu et al., "A Web 2.0 Based Scientific Application Framework," 7 pages, prior to Jul. 24, 2014.
"The Home Dashboard," CRBM info@hand website, 46 pages, prior to Apr. 25, 2013.
"Free Facilities Dashboards," eSight Energy Website, 2 pages, prior to Apr. 25, 2013.
Alerton Building Controls, Gallery Prints, 7 pages, Dec. 19, 2013.
Carter, "Industrial Energy Management Dashboards Require a Toolkit," Cross Automation, 11 pages, Nov. 4, 2013.
U.S. Appl. No. 14/169,071, filed Jan. 30, 2014.
U.S. Appl. No. 14/169,083, filed Jan. 30, 2014.
U.S. Appl. No. 14/461,188, filed Aug. 15, 2014.
U.S. Appl. No. 14/482,607, filed Sep. 10, 2014.
E-homecontrols.com, "e-Home Controls Website," link to actual website no longer works, 1 page, prior to Dec. 19, 2013.
"C&C (/)—Omniboard," 5 pages, Dec. 19, 2013. http://www.ccbac.com.
"DomController Home Automation Software—Control Anything from Anywhere," 11 pages, printed Jan. 6, 2015. http://www.domcontroller.com/en/.
"Novar Opus BAS," 1 page, prior to Feb. 13, 2013. http://www.novar.com/ems-bas/opus-building-automation-system.
"A 3D Interactive Environment for Automated Building Control," Master's Dissertation, Instituto Superior Tecnico, 120 pages, Nov. 2012.
Panduit Corp., "Enable a Building Automation with Panduit Enterprise Solutions," 4 pages, Nov. 2012.
Honeywell, "WEBs-AX Web-Enabled Building Solutions," sales brochure, Honeywell International Inc., Mar. 2009.
Honeywell, "Attune Advisory Services," press release, Honeywell International Inc., Mar. 20, 2012.
EnteliWeb Overview, web pages retrieved on May 9, 2013 from http://deltacontrols.com/products/facilities-management/supervisory-software et seq. by the Internet Archive at web.archive.org.
"BACnet Protocol Implementation Conformance Statement" for enteliWeb, Delta Controls, Jul. 17, 2013.
Castle, "7 Software Platforms that Make Building Energy Management Easy," http://greentechadvocates.com/2012/11/28/7-software-platforms-that-make-building-energy-managment-easy/, Nov. 28, 2012.
EnteliWeb "Software: Enterprise Energy Management", catalog sheet, Delta Controls, 2012.
EnteliWeb "Software: Enterprise Energy Management", catalog sheet, Delta Controls., 2010.
"Intelligent Building Management Systems in Miami," Advanced Control Corp., Mar. 7, 2013.
"The Ohio State University," BACnet International Journal, vol. 5, p. 4, Jan. 2013.
Bobker et al., "Operational Effectiveness in Use of BAS," Proceedings of the 13th International Conference for Enhanced Building Operations, Oct. 8, 2013.
Castelo, "A 3D Interactive Environment for Automated Building Control," Elsevier, Nov. 8, 2012.
"Creston Special Report: How Intelligent building management solutions are reducing operational costs," Creston, 2012.
"Building Automation Software Solutions," Iconics, 2013.
Lacey, "The Top 10 Software Vendors Connecting Smart Buildings to the Smart Grid," http://www.greentechmedia.com/articles/read/the-top-10-companies-in-enterprise-smart-grid, Jul. 18, 2013.
"NiagraAX Product Model Overview," Tridium, Inc., 2005.
"An Overview of NiagraAX: A comprehensive software platform designed to create smart device applications," Tridium, Inc., 2005.
"Phoenix Controls Portal," Phoenix Controls, Inc., 2013.
Quirk, "A Brief History of BIM," Arch Daily, Dec. 7, 2012.
Samad et al., "Leveraging the Web: A Universal Framework for Building Automation," Proceedings of the 2007 American Control Conference, Jul. 11, 2007.
Sinha et al., "9 Key attributes of energy dashboards and analytics tools," Aug. 28, 2013, https://www.greenbiz.com/blog/2013/08/28/9-key-attributes-energy-dashboards-and=analytics-tools.
Sinopoli, "Dashboards for Buildings," http://www/automatedbuildings.com/news/dec10/articles/sinopoli/101119034404sinopoli.html, Dec. 2010.
Sinopoli, "Modeling Building Automation and Control Systems," http://www.automatedbuildings.com/news/jun13/ articles/sinopoli/130521122303sinopoli.html, Jun. 2013.
Zito, "What is Tridium Part 1," http://blog.buildingautomationmonthly.com/what-is-tridium/, May 12, 2013.
Zito, "What is Tridium Part 2," http://blog.buildingautomationmonthly.com/tridium-part-2/, Sep. 10, 2013.
International Search Report and Written Opinion dated Jul. 17, 2018 for International PCT Application No. PCT/US2018/025189 (12 pages).
"Data analytics and smart buildings increase comfort and energy efficiency", https://www.microsoft.com/itshowcase/Article/Content/845/Data-analytics-and-smart-buildings-increase-comfort-and-energy-efficiency, Dec. 19, 2016, 8 pages.
Donnelly, "Building Energy Management: Using Data as a Tool", http://www.buildingefficiencyinitiative.org/sites/default/files/legacy/InstituteBE/media/Library/Resources/Existing-Building-Retrofits/Using-Building-Data-as-a-Tool.pdf, Oct. 2012, 9 pages.
"Ashrae Dashboard Research Project," 29 pages, Aug. 28, 2008.
Honeywell, "Energy Manager User Guide," Release 3.2, 180 pages, 2008.
"Fuzzy Logic Toolbox 2.1, Design and Stimulate Fuzzy Logic Systems," The MathWorks, 2 pages, May 2004.
"Junk Charts, Recycling Chartjunk as junk art," 3 pages, Oct. 2, 2006.
"Model Predictive Control Toolbox 2, Develop Internal Model-Based Controllers for Constrained Multivariable Processes," The MathWorks, 4 pages, Mar. 2005.
Honeywell, "Product Guide 2004," XP-002472407, 127 pages, 2004.
"Statistics Toolbox, for Use with Matlab," User's Guide Version2, The MathWorks, 408 pages, Jan. 1999.
"Vykon Energy Suite Student Guide," Tridium Inc., 307 pages, Mar. 3, 2006.
"Web Based Energy Information Systems for Energy Management and Demand Response in Commercial Buildings," California Energy Commission, 80 pages, Oct. 2003.
Andover Controls, Network News, vol. 2, No. 2, 8 pages, 1997.
Andover Controls World, 4 pages, Spring 1997.
Bell et al., "Early Event Detection—Results from A Prototype Implementation," AICHE Spring National Meeting, 15 pages, Apr. 2005.
Cadgraphics, "The Cadgraphics User's Guide," 198 pages, 2003.
Carrier Comfort Network CCN Web, "Web Browser User Interface to the Carrier Comfort Network," 2 pages, 2002.
Carrier Comfort Network CCN Web, Overview and Configuration Manual, 134 pages, Apr. 2006.
Carrier Comfort Network CCN Web, Product Data, 2 pages, Apr. 2006.
Carrier, "i-Vu Powerful and Intuitive Front End for Building Control," 2 pages, Aug. 2005.
Carrier, "i-Vu Web-Based Integrated Control System," 3 pages, 2005.
Carrier, Demo Screen Shots, 15 pages, prior to Aug. 27, 2007.
Carrier, i-Vu CCN 4.0, Owner's Guide, 20 pages, Jul. 2007.
Carrier, i-Vu CCN, 7 pages, 2007.
Chan, "Rank Revealing QR Factorizations," Linear Algebra and It's Applications, vol. 88-89, p. 67-82, Apr. 1987.
Circon, "i-Browse Web-Based Monitoring and Control for Facility Management," 2 pages, prior to Aug. 27, 2007.
Australian Application 2009904740, Published copy, 28 pages, Application Filed on Sep. 29, 2009.

(56) References Cited

OTHER PUBLICATIONS

Echelon, "Energy Control Solutions with the i.Lon SmartServer," 4 pages, 2007.
Echelon, "i.Lon 100e3 Internet Server Models 72101R-300, 72101R-308, 72102R-300, 72103-R300 . . . " 5 pages, copyright 2002-2007.
Echelon, "i.Lon 100e3 Internet Server New Features," 15 pages, Sep. 2006.
Echelon, "i.Lon SmartServer," 5 pages, 2007.
Honeywell News Release, "Honeywell's New Sysnet Facilities Integration System for Boiler Plant and Combustion Safety Processes," 4 pages, Dec. 15, 1995.
Honeywell, "Excel Building Supervisor-Integrated R7044 and FS90 Ver. 2.0," Operator Manual, 70 pages, Apr. 1995.
Honeywell Home and Building Control Bulletin, "Introduction of the S7350A Honeywell WebPAD Information Appliance," 2 pages, Aug. 29, 2000; Picture of WebPad Device with touch screen, 1 Page; and screen shots of WebPad Device, 4 pages.
Honeywell, Excel 15B W7760B Building Manager Release 2.02.00, Installation Instructions, 28 pages, Dec. 2004.
Honeywell, The RapidZone Solution, Excel 5000 Open System, Application Guide, 52 pages, Jan. 2004.
"Remote Building Monitoring and Operations Home Page," 5 pages, prior to Aug. 27, 2007.
"Carrier: i-Vu CCN," 1 page, printed Mar. 11, 2008.
Carrier: 33CSCCNWEB-01 CCN Web Internet Connection to the Carrier Comfort Network, 1 page, printed Mar. 11, 2008.
"Products," 5 pages, printed Jul. 3, 2007. http://www.docs.hvacpartners.com/idc/groups/public/documents/techlit/gs-controls-ivuccn.rtf.
Lightstat Incorporated, "Internet Programmable Communicating Thermostats," 1 page, printed Mar. 13, 2007. http://www.lightstat.com/products/istat.asp.
Sharp, "Actius RD3D Desktop Replacement Notebook with Industry-Breakthrough 3D Screen," 1 page, printed Jun. 16, 2005. http://www.sharpsystems.com/products/pc_notebooks/actius/rd/3d/.
"Lights on a Wireless Lighting Control System," 11 pages, printed Mar. 22, 2007 http://www2.sims.berkeley.edu/courses/is213/s06/projects/lightson;final.html.
I.Lon 100e3 Internet Server, 1 page, prior to Aug. 27, 2007.
I.Lon, SmartServer, 2 pages, prior to Aug. 27, 2007.
I-stat, Demo Screen Shots, 9 pages, printed Mar. 13, 2007.
I-stat, The Internet Programmable Thermostat, 2 pages, prior to Aug. 27, 2007.
Ball, "Green Goal of 'Carbon Neutrality' Hits Limit," TheWall Street Journal, 7 pages, Dec. 30, 2008.
Network Integration Engine (NIE), Johnson Controls, 3 pages, Nov. 9, 2007.
Network Integration Engine (NIE), Product Bulletin, Johnson Controls, pp. 1-11, Jan. 30, 2008.
Kourti, "Process Analysis and Abnormal Situation Detection: From Theory to Practice," IEEE Control Systems Magazine, p. 10-25, Oct. 2002.
Mathew, "Action-Oriented Benchmarking, Using CEUS Date to Identify and Prioritize Efficiency Opportunities in California Commercial Buildings," 26 pages, Jun. 2007.
Morrison et al., "The Early Event Detection Toolkit," Honeywell Process Solutions, 14 pages, Jan. 2006.
Narang, "Webarc: Control and Monitoring of Building Systems Over the Web," 53 pages, May 1999.
Olken et al., "Object Lessons Learned from a Distributed System for Remote Building Monitoring and Operation," ACM SIGPLAN Notices, vol. 33, No. 10, pp. 284-295, Oct. 1998.
Proliphix, Inc., "Proliphix IP Devices: HTTP API," 28 pages, Jan. 23, 2006.
Proliphix, Inc., "Remote Management User Guide," 12 pages, prior to Aug. 27, 2007.
Rogan et al., "Smart and Final Food Stores: A Case Study in Web Based Energy Information and Collection," Web Based Energy Information and Control Systems: Case Studies and Application, Chapter 6, p. 59-64, 2005.
Sharp, "Actius AL3DU 3D LC Display High Performance 3D Visualization," 2 pages, prior to Mar. 17, 2006.
So et al., "Building Automation on the Information Superhighway," Ashrae Transactions, vol. 104, Part 2, pp. 176-191, 1998.
So et al., "Building Automation Systems on the Internet," Facilities vol. 15, No. 5/6, pp. 125-133, May/Jun. 1997.
Talon, "Raptor Controller," 6 pages, Oct. 2003.
Talon, "Workstation Software," 4 pages, Nov. 2002.
Trane, "System Programming, Tracer Summit Version 14, BMTW-SVP01D-EN," 623 pages, 2002.
Lucid Design Group, Inc., "Building Dashboard," 2 pages, Printed May 30, 2013.
"America's Largest Managed Security Services Provider Launches Comprehensive, Integrated Covid-19 Safety Program for Office Buildings and Suites," KastleSafeSpaces, 5 pages, May 11, 2020.
"Biometric Door Reader With Body Temperature Detection," Kintronics, 9 pages, accessed May 21, 2020.
"Body Surface Temperature Screening with Alarm Function TVS-200IS/TVS-500IS," Nippon Avionics Co., 3 pages, accessed May 21, 2020.
"BriefCam announces video analytics innovation for contact tracing, physical distancing, occupancy management and face mask detection," BriefCam LTD, 11 pages, Jun. 5, 2020.
"Thermal Imaging SmartPhone can be used for Temperature Screening of People," CAT, 3 pages, accessed Jul. 13, 2020.
"Contact Tracing Now Available on Identiv's Hirsch Velocity Access Control Platform," Identiv, 5 pages, May 21, 2020.
Silva et al., "Cough localization for the detection of respiratory diseases in pig houses," ScienceDirect, 7 pages, May 28, 2008.
Oey et al., "Evaluation of Isolation Compliance Using Real Time Video in Critical Care," North Shore University Hospital, 1 page, Oct. 9, 2015.
"Facial Attendace System With Temperature Screening Now in India," IANS, 5 pages, Mar. 19, 2020.
"Plan to Re-Open," Ehigh, 16 pages, accessed Jun. 13, 2020.
"How Smarter AI-Powered Cameras Can Mitigate the Spread of Wuhan Novel," AnyConnect, 22 pages, 2020.
"How to fight COVID-19 with machine learning," DataRevenue, 20 pages, accessed May 25, 2020.
Honeywell, "Inncontrol 5," 2 pages, Aug. 8, 2018.
"IP Door Access Control," Kintronics, 21 pages, 2014.
"Kogniz AI Health Response Platform," Kogniz, 9 pages, accessed May 21, 2020.
"Machine Learning Could Check if You're Social Distancing Properly at Work," MIT Technology Review, 7 pages, Apr. 17, 2020.
Punn et al., "Monitoring COVID-19 social distancing with person detection and tracking via fine-tuned Yolo v3 and Deepsort techniques," 10 pages, May 6, 2020.
Burt, "NEC launches dual face biometric and fever detection system for access control," Biometric Update, 4 pages, May 8, 2020.
"Remote temperature monitoring," AXIS Communication, 10 pages, 2014.
"FebriEye-AI Based Thermal Temperature Screening System," vehant, 1 page, 2020.
"See The World in a New Way Hikvision Thermal Cameras," Hikvision, 12 pages, 2017.
Allain, "Trying out the iPhone Infrared Camera: The FLIR One," Wired, 15 pages, 2014.
Dasgupta, "Your voice may be able to tell you if you have Covid," Hindustan Times, 4 pages, Apr. 16, 2020.
Ganguty, "Gurugram-based startup Staqu has modified AI-powered Jarvis to battle coronavirus," Yourstory, 7 pages, Mar. 31, 2020.
Trane, "Creating Input/Output Objects," 196 pages, retrieved Jul. 10, 2020.
Trane, "Using the Graphing Control Editor," 181 pages, retrieved Jul. 10, 2020.
Extended European Search Report, EP Application No. 21177865.9, Nov. 17, 2021 (7 pgs).
Examination Report No. 3 for Standard patent application, AU Patent Application No. 2021203457, AU Patent Office, Nov. 3, 2022 (3 pages).

\* cited by examiner

DEVICES, SYSTEMS, AND METHODS FOR ASSESSING FACILITY COMPLIANCE WITH INFECTIOUS DISEASE GUIDANCE

This application claims the benefit of U.S. Provisional Application No. 63/042,389, filed Jun. 22, 2020, which is hereby incorporated by reference.

TECHNICAL FIELD

The present disclosure relates generally to devices, methods, and systems for monitoring building performance. More particularly, the present disclosure relates to devices, methods, and system for monitoring facility compliance with infectious disease guidance.

BACKGROUND

Coronavirus disease 2019 (COVID-19) is an infectious disease caused by severe acute respiratory syndrome coronavirus 2 (SARS-CoV-2). COVID-19 is one of many infectious diseases transmitted via airborne particles. In some cases, it may be difficult to mitigate the spread of infectious diseases, particularly diseases transmitted through airborne particles, at indoor facilities (e.g., buildings, department stores, warehouses, plants, factories, refineries, airports, laboratories, school buildings, theaters, etc.) due to the indoor environment, proximity of occupants, and/or other factors. Often, these indoor facilities have various building automation systems (e.g., heating, ventilation, and air conditioning (HVAC) systems, surveillance systems, security systems, energy management systems, etc.) to control environmental conditions of the indoor facility and/or monitor occupancy.

SUMMARY

The present disclosure generally relates to monitoring compliance with prescribed guidance, and more particularly, to monitoring compliance of a facility with infectious disease guidance.

In one example, a method for achieving compliance with infectious disease guidance for reducing airborne disease transmission in a facility is provided, where the infectious disease guidance may include a plurality of recommendations that can be assessed by a plurality of sensing devices. The method may include sensing a plurality of conditions in the facility using the plurality of sensing devices, determining a compliance parameter for two or more of the plurality of recommendations of the infectious disease guidance based at least in part on one or more of the plurality of sensed conditions, determining an individual score for each of the determined compliance parameters, determining an overall score of the facility by aggregating the individual scores associated with each of the two or more of the plurality of recommendations, and displaying a dashboard on a display that includes the overall score as well as one or more of the individual scores. Each of the individual scores may provide a measure of how well the corresponding compliance parameter is considered to satisfy the corresponding recommendation of the infectious disease guidance.

In another example configuration, a non-transient computer readable medium storing instructions that when executed by a processor may cause the processor to receive a plurality of sensed conditions in a facility sensed by a plurality of sensing devices, determine a compliance parameter for at least two recommendations of an infectious disease guidance based at least in part on one or more of the plurality of sensed conditions, determine an individual score for each of the determined compliance parameters, and display on a display one or more of the individual scores. Each of the individual scores provide a measure of how well the corresponding compliance parameter is considered to satisfy the corresponding recommendation of the infectious disease guidance.

In a further example configuration, a system for accessing compliance with infectious disease guidance for reducing airborne disease transmission in a facility is provided, where the infectious disease guidance may include a plurality of recommendations that can be assessed by one or more sensing devices. The system may include memory for storing a plurality of conditions in the facility sensed by a plurality of sensing devices and a controller operatively coupled to the memory. The controller may be configured to determine a compliance parameter for two or more of the plurality of recommendations of the infectious disease guidance based at least in part on one or more of the plurality of sensed conditions, determine an individual score for each of the determined compliance parameters, assign an individual score of zero to a compliance parameter for one or more of the plurality of recommendations that cannot be determined because the memory does not currently store a condition from which the corresponding compliance parameter can be determined, and display on a display one or more of the individual scores including one or more of individual scores corresponding to the compliance parameters that cannot be determined to encourage an installation of one or more sensing devices that can sense a condition from which the compliance parameters that could not be determined can be determined. Each of the individual scores may provide a measure of how well the corresponding compliance parameter is considered to satisfy the corresponding recommendation of the infectious disease guidance.

DESCRIPTION

Figure 1:
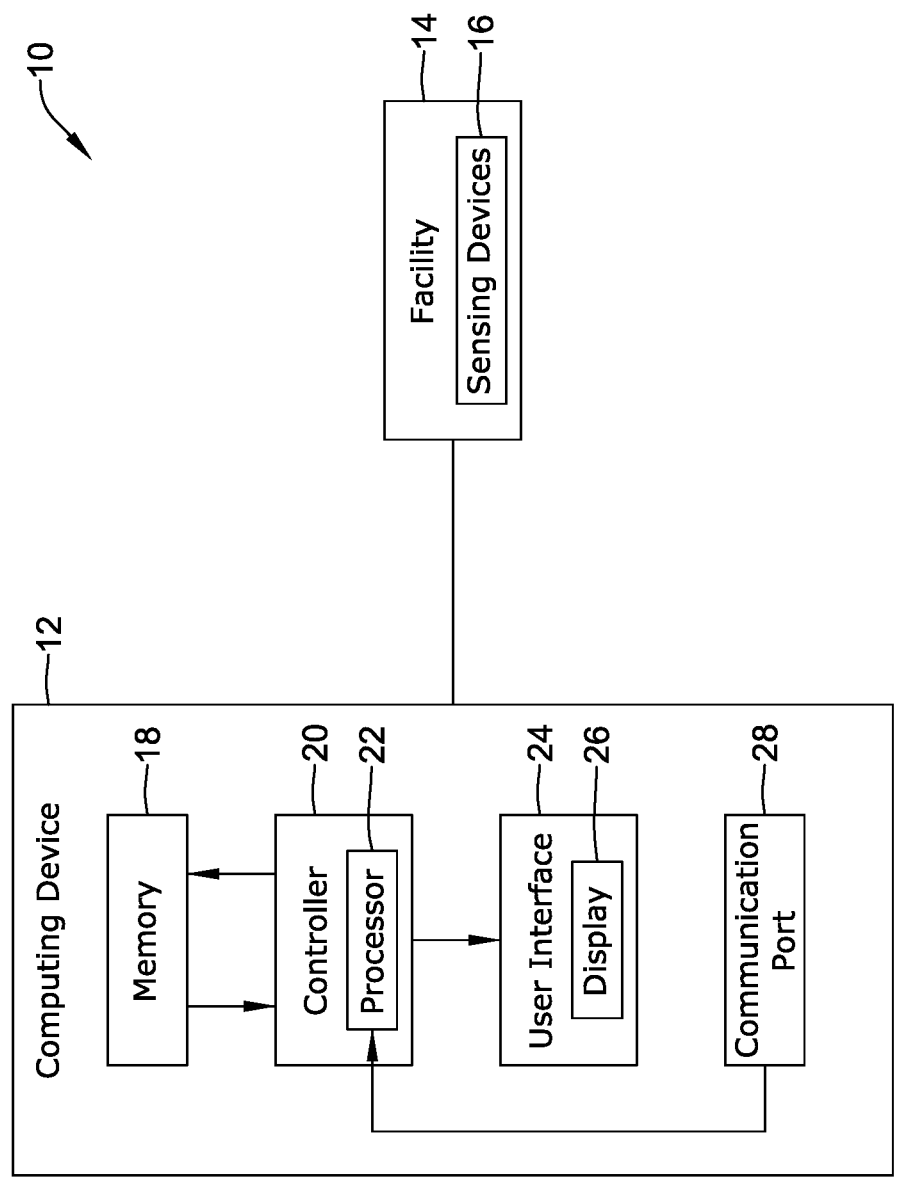
FIG. 1 is schematic block diagram of an illustrative system for monitoring compliance of a facility with infectious disease guidance.

The present system and approach may incorporate one or more processors, computers, controllers, user interfaces, wireless and/or wire connections, and/or the like, in an implementation described and/or shown.

Facilities often include building automation systems (e.g., heating, ventilation, and air conditioning (HVAC) systems, surveillance systems, security systems, energy management systems, etc.). Various organizations worldwide (e.g., government organizations, educational organizations, etc.) have provided guidelines on how to operate building automation system to reduce risk of airborne disease transmissions within facilities. Similarly, various organizations worldwide have provided guidelines on how occupants of a facility and monitoring occupancy can reduced risk of airborne disease transmission. Other guidelines relating to facilities and transmission of infectious disease are contemplated and may be adapted and used, depending on the facility.

It is difficult for facility managers to assess performance of their facilities, occupants, etc. against guidance (e.g. guidelines, rules, etc.). In some cases, the guidance may specify desired environmental conditions and desired occupancy/occupant behavior to help reduce or mitigate risk of airborne disease transmission in a facility. Additionally, in view of various guidelines from various organizations, it has been difficult for facility managers to assess whether their facilities have the necessary sensor devices and/or other suitable sensing or monitoring equipment to accurately judge and/or reduce the risk of airborne disease transmission.

This disclosure provides methods and systems for assessing a facilities compliance with various guidelines related to reducing risk of infectious disease (e.g., COVID-19, Ebola, influenza, airborne diseases, and/or other infectious diseases) transmissions. Sensing devices of existing building automation systems and/or other suitable sensing devices may be utilized. In some cases, methods and systems are provided to help facility managers identify when additional sensors, cameras, and/or other equipment may help in mitigating risk of transmitting infectious diseases in their facility, and in some cases, may quantify how much such additional equipment may help mitigate the risk of transmission of infectious diseases in their facility.

The techniques and/or systems disclosed herein may provide displays offering facility managers easily understandable performance metrics of a facility and/or facility occupants against a set of infectious disease guidelines. The metrics may incorporate and/or be based on knowledge of a facility location (e.g., geographic location), knowledge of a facility size, knowledge of a facility floorplan, knowledge of sensing devices at a facility, knowledge of common HVAC system capability and parameters, adjustable values or weights that may be tuned based on climate, building characteristics, evolving knowledge (e.g., guidelines, studies, laws, etc.) related to airborne disease transmission, etc.

FIG. 1 depicts a schematic block diagram of an illustrative system 10 for monitoring compliance of a facility with infectious disease guidance. As discussed above, the infectious disease guidance may include one or more recommendations to mitigate airborne disease transmission within a facility. Example recommendations may include recommendations related to values, counts, percentages, and/or other measures of one or more of relative humidity in a facility, $CO_2$ concentration in a facility, air change rates in a facility, occupancy in a facility, particulate matter concentrations in a facility, total volatile organic compound (TVOC) concentrations in a facility, a maximum occupancy level in a facility, maximum occupancy density in a facility, a number of crowd incidents per day in the facility, a percent of health related standard operating procedure actions that have been closed, mask compliance in a facility, elevated body temperature incidents in the facility, number of people potentially exposed to an infected individual in the facility determined via contact tracing, and/or recommendations related to one or more other suitable factors affecting airborne disease transmission within a facility.

The system 10 may include, but is not limited to, one or more computing devices 12 and one or more facilities 14. Although the computing device 12 may be depicted in FIG. 1 as being separate from the facility 14, one or more of the computing devices 12 may be part of or within one or more facilities 14. In some case, the system 10 may not include the one or more facilities 14 and instead be in communication with the facilities 14 (e.g., in communication with the facilities and/or components thereof) and/or otherwise receive data related to the facilities 14 from the facilities 14 and/or a third party.

The one or more facilities 14 may be any suitable type of facility 14. Example types of facilities 14 include, but are not limited to, buildings, department stores, warehouses, plants, factories, refineries, airports, laboratories, office buildings, school buildings, theaters, arenas, stadiums, hotels, dorms, lecture halls, restaurants, etc.

The one or more facilities may include one or more sensing devices 16. Although not required, the one or more sensing devices may be part of a building automation system. A building automation system may include one or more of HVAC systems, surveillance systems, security systems, energy management systems, etc. In some cases, the sensing devices 16 may be part of a closed loop control of building automation system components, such that the components of the building automation system may be controlled in response to outputs (e.g., sensed measurements) from the sensing devices 16.

The sensing devices 16 may include any suitable sensing devices configured to sense measures related to one or more parameters that may facilitate assessing compliance with guidance or recommendations for reducing and/or mitigating risk of airborne disease transmissions in the facilities 14. Example sensing devices 16 may include, but are not limited to, an occupancy sensor, a video camera, a control signal monitor (e.g., to monitor when and/or how devices affecting infectious disease are used, such as UV lights, air exchangers, fans, etc.), an air sensor, a humidity sensor, a temperature sensor, a $CO_2$ sensor, a thermostat, a particulate matter sensor, a TVOC sensor, video cameras, still cameras, identification card readers, thermometers, infrared sensors, pressure sensors (e.g., to monitor and/or effect pressure zones configured to exchange air in a specified zone in a facility), etc.

The computing device 12 may be any suitable type of computing device. In some cases, the computing device 12 may be incorporated into one or more other electronic devices and/or there may be a plurality of computing devices 12. Additionally or alternatively, one or more features of the computing device 12 may be incorporated in the electronic devices (e.g., the sensing devices 16, etc.) discussed herein to facilitate operation of the electronic device and/or communication with other electronic devices.

The computing device 12 may be and/or may be part of, for instance, a smart phone, a tablet, a personal digital assistant (PDA), a personal computer, a beacon, a camera, a display device, a video recorder, a network component, a server, and/or other suitable computing device. In some cases, the computing device 12 may be distributed amount two or more devices. Configurations of the present disclosure are not limited to a particular type of computing device 12. In some cases, the computing device 12 may include memory 18, a controller 20, one or more processors 22, one or more user interfaces 24, one or more displays 26, one or more communication ports 28, and/or one or more other suitable computing components.

As shown in FIG. 1, the memory 18 and the controller 20 may communicate with one another such that the controller 20 and/or a processor 22 thereof or separate therefrom may execute instructions (e.g., application program code of a mobile application or software, among other instructions) stored on the memory 18. Although not depicted in FIG. 1, the controller 20 may include at least part of the memory 18 and that part of the memory 18 may include instructions stored thereon for execution by the processor 22.

The memory 18 may be any type of storage medium that can be accessed by the controller 20 and/or the processor 22 to perform various examples of the present disclosure. The memory 18 may be may be volatile or nonvolatile memory. Additionally or alternatively, the memory 18 may be configured to store data and/or information in one or more databases.

The memory 18 may also be removable (e.g., portable) memory, or non-removable (e.g., internal) memory. For example, the memory 18 may be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disk read-only memory (CD-ROM)), flash memory, a laser disk, a digital versatile disk (DVD) or other optical disk storage, and/or a magnetic medium such as magnetic cassettes, tapes, or disks, among other types of memory.

Further, although the memory 18 is illustrated as being located in the computing device 12, embodiments of the present disclosure are not so limited. For example, the memory 18 may also be located internal to another computing resource (e.g., enabling computer readable instructions to be downloaded over the Internet or another wired or wireless connection).

The controller 20 of the computing device 12 may include one or more processors 22. For example, the controller 20 may include a single processor or more than one processor working individually or with one another (e.g., dual-core, etc.). In some cases, the controller 20 may include at least a portion of the memory 18. The controller 20 and/or the processor 22 may be configured to execute instructions, including instructions that may be loaded into the memory 18 and/or other suitable memory. Example processor components may include, but are not limited to, microprocessors, microcontrollers, multi-core processors, graphical processing units, digital signal processors, application specific integrated circuits (ASICs), field programmable gate arrays (FPGAs), discrete circuitry, and/or other suitable types of data processing devices.

The user interface 24, when provided, may be any suitable user interface and/or user interface components configured to facilitate a user of the computing device 12 interacting with the computing device 12 via the user interface 24. For example, the user interface 24 may be used to provide information to and/or receive information from the user of the computing device 12 or system 10. For instance, the user interface 24 may receive selections of parameters, receive selections of parameter weights, output a dashboard depicting parameter values, output alarms, output video, etc. The user interface 24 may include a keyboard or keyboard functionality, a pointer (e.g., a mouse, touch pad, or touch ball) or pointer functionality, a microphone, a speaker, a light system, a haptic system, a camera, a video camera, and/or other suitable user interface features the user may use to input information into and/or receive information from the computing device 12. Configurations of the present disclosure, however, are not limited to a particular type(s) of user interface 24.

In some cases, the user interface 24 may include a graphical user interface (GUI) that may have a display 26 (e.g., a screen) that may provide and/or receive information to and/or from the user of the computing device 12. The display 26 may be, for instance, a touch-screen (e.g., the GUI may include touch-screen capabilities).

The communications port 28 may be any type of communication port(s) and may facilitate wired and/or wireless communication with one or more networks. In one example, the communications port 28 may facilitate communication with one or more networks and/or other devices (e.g., facilities, other computing devices, mobile devices, servers, and/or other suitable devices) through any suitable connection including, but not limited to, radio communication, Ethernet, cellular communication, ZigBee, REDLINK™, Bluetooth, Bluetooth Low Energy (BLE), WiFi, IrDA, dedicated short range communication (DSRC), EnOcean, Near Field Communication (NFC), and/or any other suitable common or proprietary wired or wireless protocol. In one example, the communications port 28 may at least include a port configured to communicate over one or more network connections with one or more of the sensing devices 16 and/or with other computing devices to receive infectious disease guidance.

Figure 2:
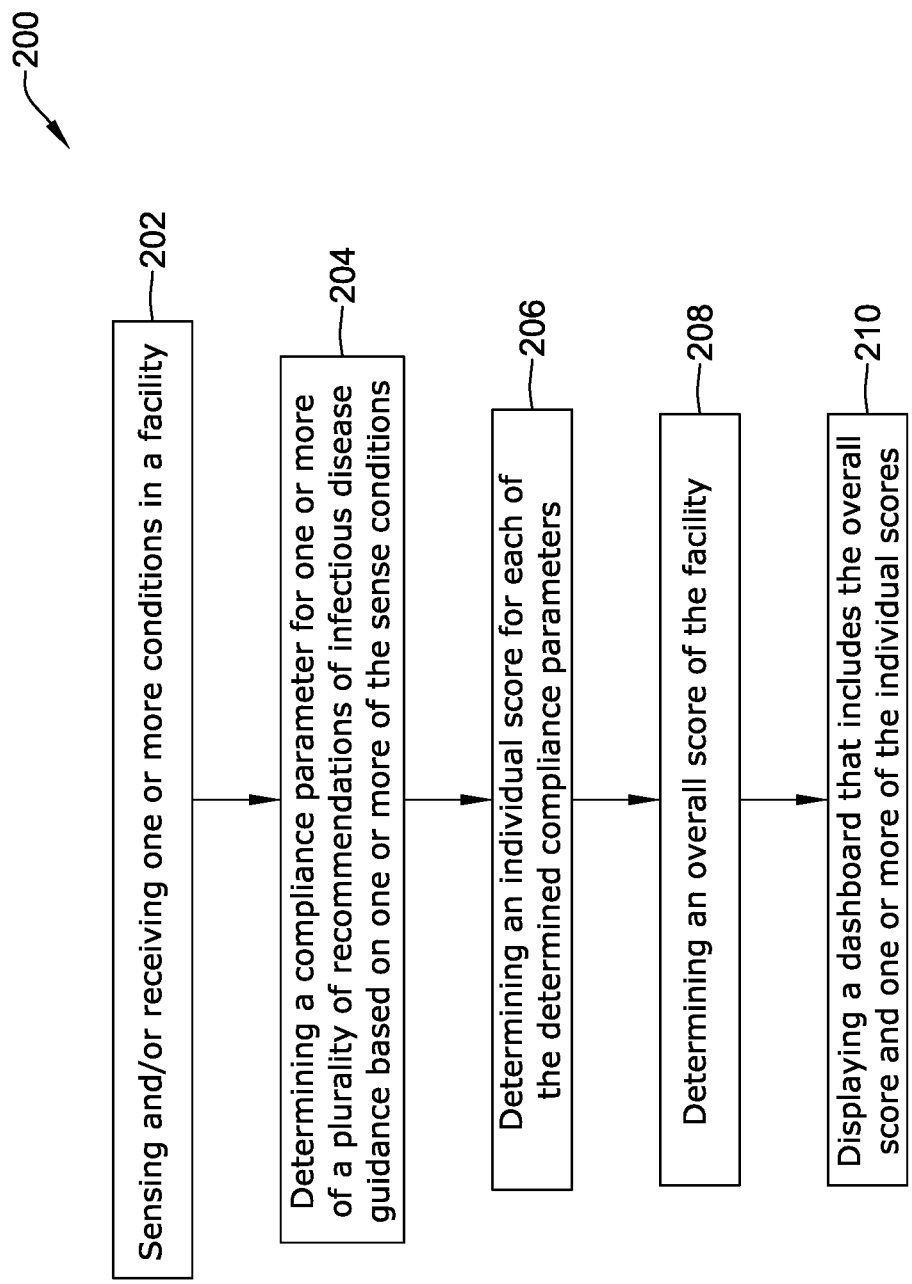
FIG. 2 is a flow diagram of an illustrative method of assessing facility compliance with infectious disease guidance.

FIG. 2 is a schematic flow diagram of an illustrative method 200 for assessing compliance of one or more facilities (e.g., a single facility and/or a group of facilities where facilities may be grouped to compare one to another) with infectious disease guidance and/or recommendations for reducing airborne disease and/or other infectious disease transmissions in a facility, where the guidance and/or recommendations may include one or more recommendations that can be assessed using measurements from the sensing devices 16. Although the method 200 for assessing compliance with infectious disease guidance and/or recommendations is depicted as including various steps, additional, alternative, intermediary, and/or sub-steps may be utilized.

The method 200 may include sensing and/or receiving 202 one or more conditions in a facility (e.g., the facility 14 and/or one or more other suitable facilities). In some cases, the one or more conditions may be sensed using sensing devices (e.g., the sensing device 16 and/or other suitable sensing devices) in a facility or in communication with the facility or components thereof. In one example, measures indicative of conditions in a facility may be provide to a computing from the sensing devices. The computing device (e.g., the computing device 12 and/or other suitable computing device) may be or may include a work station, a mobile device, a remote server, and/or other suitable computing device. In some cases, the measures from the sensing devices may be stored in a database in memory (e.g., the memory 18 and/or other suitable memory) of or in communication with the computing device.

With the one or more conditions in the facility sensed and/or received, one or more compliance parameters for one or more of a plurality of recommendations of the infectious disease guidance may be determined 204. The plurality of recommendations may be stored in memory (e.g., the memory 18 and/or other suitable local or remote memory) and/or obtained via a communications port (e.g., the communications port 28 and/or other suitable communications port).

In some cases, the one or more compliance parameters may be determined 204 based, at least in part, on one or more of the plurality of sensed conditions. Further, compliance parameters may be determined for parameters even if a facility does not current have a sensing device that can sense a condition from which a corresponding compliance parameter can be determined. In such a case, and in one example, these compliance parameters may be given a zero value or other nominal value when a sensing device is not available to sense and/or provide a condition related to the parameter. This may provide a queue to the facility manager that obtaining such a sensing device may help mitigate risk of transmitting infectious diseases in their facility, and in some cases, may quantify how much such additional equipment may help mitigate the risk of transmission of infectious diseases in their facility.

In one example of determining a compliance parameter, when a facility includes sensing devices configured to sense humidity levels, $CO_2$ levels, air exchanges, occupancy, particulate matter, and TVOC, determining a compliance parameter may include determining values of a relative humidity percentage, parts per million of $CO_2$, a number of air exchanges per hour, a percent occupancy of a total allowed occupancy, a particulate matter measurement, and a TVOC measurement. In another example of determining a compliance parameter, when a facility includes sensing configured to sense occupancy levels, occupancy locations, crowd incidents, standard operating procedure compliance, mask-wearing compliance, body temperature, contact tracing, determining a compliance parameter may include determining values of a percent occupancy of a total allowed occupancy, occupancy density per square unit, a number of incident per day, a percent of invoked standard operating procedures that were closed in a day, mask-wearing compliance, elevated body temperature compliance, and a number of persons exposed to an infectious disease per day. Although the determined compliance parameters may be the raw value measured by the sensor device and/or calculated or determined from measurements of the sensor device, the compliance parameters may be determined based, at least in part, on other sensed and/or or received conditions and/or other data.

An individual score may be determined for each of the determined compliance parameters, as shown at 206. For example, to determine a score for a relative humidity compliance parameter, the compliance parameter (e.g. sensed relative humidity) may be compared to a set of ranges for relative humidity set forth in the infectious disease guidance and/or recommendations, where each range has a score associated therewith. In the example, the infectious disease guidance and/or recommendations may indicate that for mitigating risk of airborne infectious disease transmission it is most preferable to have a relative humidity level between 40% and 60% RH, it is next most preferable to have a relative humidity level between 60% and 70% RH, it is next most preferable to have a relative humidity level above 70% RH, it is next most preferable to have a relative humidity level between 30% and 40% RH, and least preferable to have a relative humidity level less than 30% RH. In one example, the score may be set on a 9 point scale, wherein 9 is the best or highest score. For example, a score of nine (9) is given when the compliance parameter value (e.g. sensed relative humidity) is within the most-optimal range of 40% and 60% RH, a score of seven (7) is given when the compliance parameter value (e.g. sensed relative humidity) is within the next most optimal range of 60% and 70% RH, a score of five (5) is given when the compliance parameter value (e.g. sensed relative humidity) is within the next most optimal range of above 70%, a score of three (3) is given when the compliance parameter value (e.g. sensed relative humidity) is within the next most optimal range of 30% and 40% RH, and a score of one (1) is given when the compliance parameter value (e.g. sensed relative humidity) is within the least desirable range of less than 30% RH.

In some cases, a compliance parameter may not be able to be determined even though the infectious disease guidance and/or recommendations provide a recommendation for the condition or parameter. For example, if the guidance and/or recommendations provide a recommendation for occupancy levels relative to a maximum occupancy (e.g., 50%), but a facility does not have a manner of determining occupancy, it may not be able to determine a compliance parameter value for the condition/parameter. In such instances, an individual score of zero (0) may be assigned to the compliance parameters for which a facility does not have a sensing device that can sense a condition from which the compliance parameter may be determined.

Although not required, the scores may be weighted to give different weights to different compliance parameters. The weights may be applied in any suitable manner. In one example, compliance parameters that are considered to be more important or effective in reducing risk of airborne disease transmissions within the facility may have a greater weight than other compliance parameters that are considered less important or less effective. In another example, all compliance parameters may be weighted equally. In some cases, the weights may be user definable.

An example calculation for determining a weighted individual score for relative humidity having an initial score of five (5) (e.g., at 75% relative humidity) may be done. Relative humidity settings may be viewed as having a great importance for impacting risk of infectious disease transmission within a facility and as a result, may be given a high weight of nine (9) (e.g., on a nine (9) point scale). In the example calculation, the compliance parameter of relative humidity may have a weighted individual score of 45 (e.g. the initial score of 5 times the assigned weight of 9).

Figure 4:
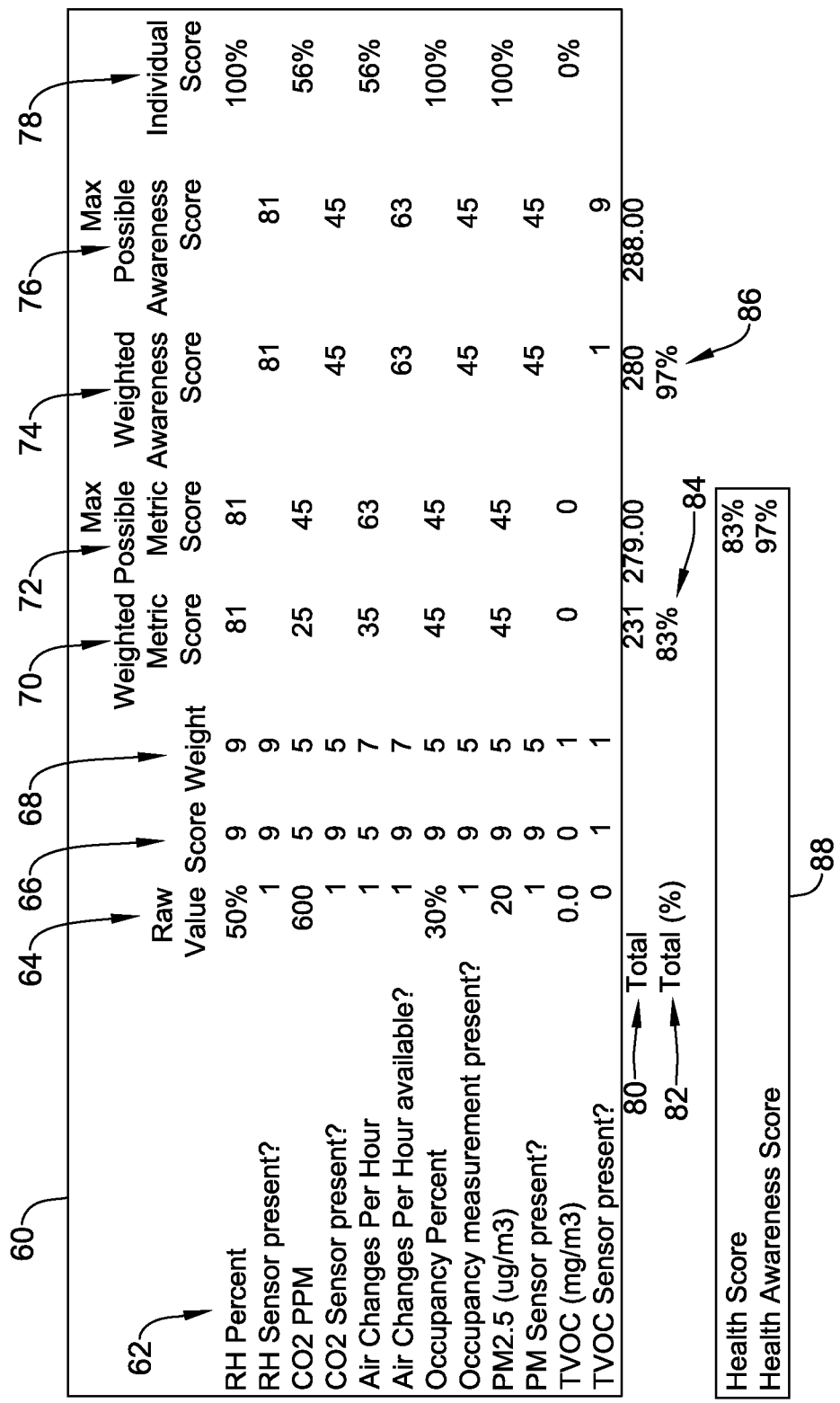
FIG. 4 is a schematic diagram of illustrative parameters and parameter values that may be used to produce the display illustrated in FIG. 3.
Figure 6:
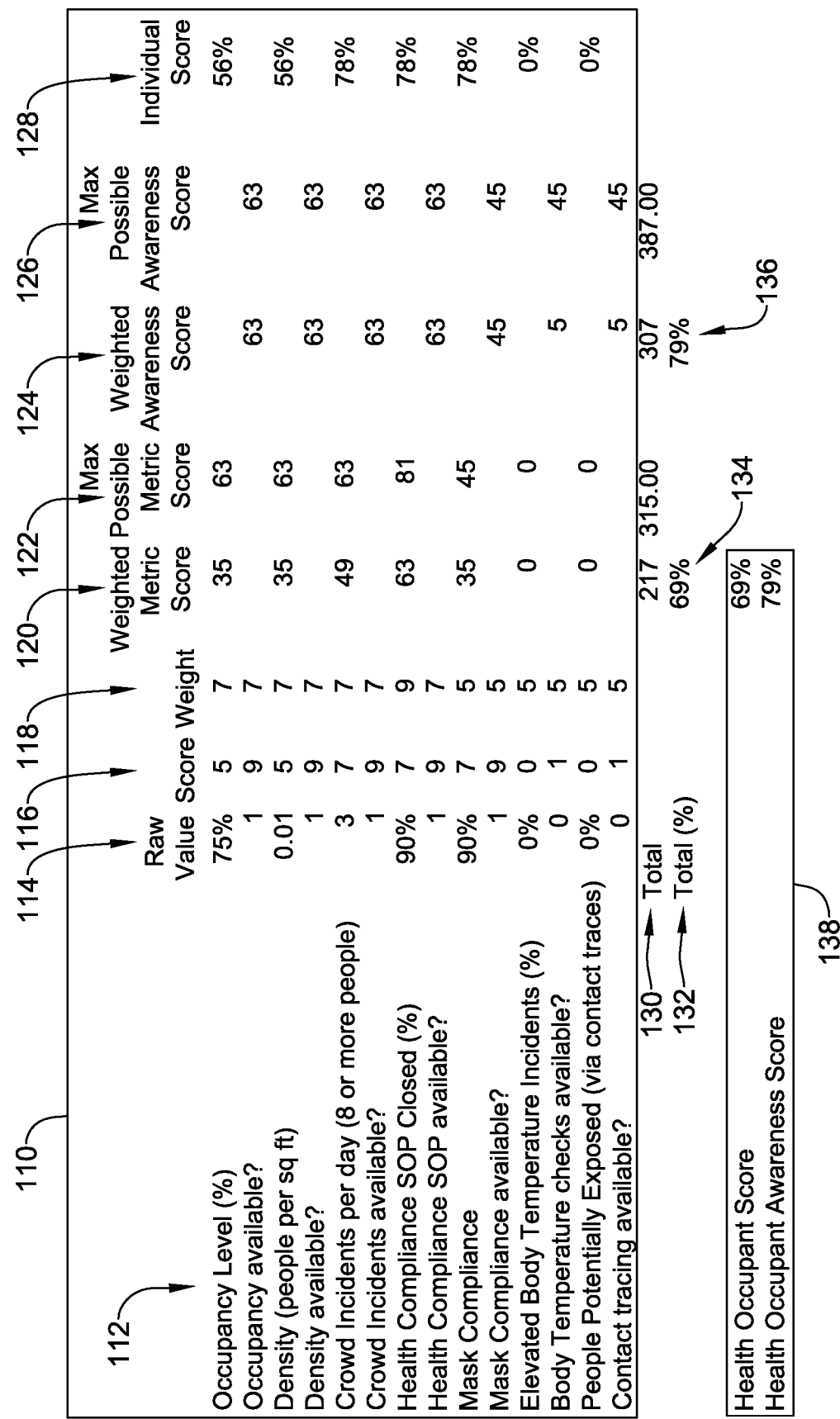
FIG. 6 is a schematic diagram of illustrative parameters and parameter values that may be used to produce the display illustrated in FIG. 5.

In some cases, the individual scores for each of the compliance parameters may be scaled to be a percentage (e.g., a value between 0% and 100%), where the percentage may be a value of the compliance parameter relative to a maximum value for the compliance parameter. For example, when the compliance parameter is scored (e.g., on a (9) point scale, as discussed above, or other suitable scale), the individual score for a determined compliance parameter may be the determined compliance parameter score divided by nine (9) (e.g., the maximum value). In another example, when the compliance parameter is scored (e.g., on a nine (9) point scale, as discussed above, or other suitable scale) and weighted (e.g., on a nine (9) point scale, as discussed above, or other suitable scale), the scaled weighted individual score for a determined compliance parameter may be the weighted determined compliance parameter divide by eighty one (81) (e.g., the maximum weighted value). Other suitable techniques may be utilized to calculate or otherwise determine the individual score of the determined compliance parameters expressed as a percentage. FIGS. 4 and 6 provide example values associated with determining individual scores for compliance parameters related to infectious disease guidance and/or recommendations.

The method 200 may further include determining 208 an overall score of the facility (or part of a facility). In some cases, the overall score of the facility may be determined by aggregating the individual scores associated with each of the determined compliance parameters associated with the infectious disease guidance and/or recommendations. For example, determining the overall score by aggregating the individual scores for the determined compliance parameters may include, but are not limited to, adding the unweighted individual scores for the determined compliance parameters together, adding the weighted individual scores for the determined compliance parameters together, adding the unweighted individual scores for the determined compliance parameters and dividing by a sum of the maximum unweighted values of individual scores for the determined compliance parameters, adding the weighted individual scores for the determined compliance parameters and dividing by a sum of the maximum weighted values of individual scores for the determined compliance parameters, averaging individual scores for the determined compliance parameters that are represented by averages, and/or aggregating in one or more other suitable manners. FIGS. 4 and 6 depict example values associated with determining the overall score of the facility.

Figure 3:
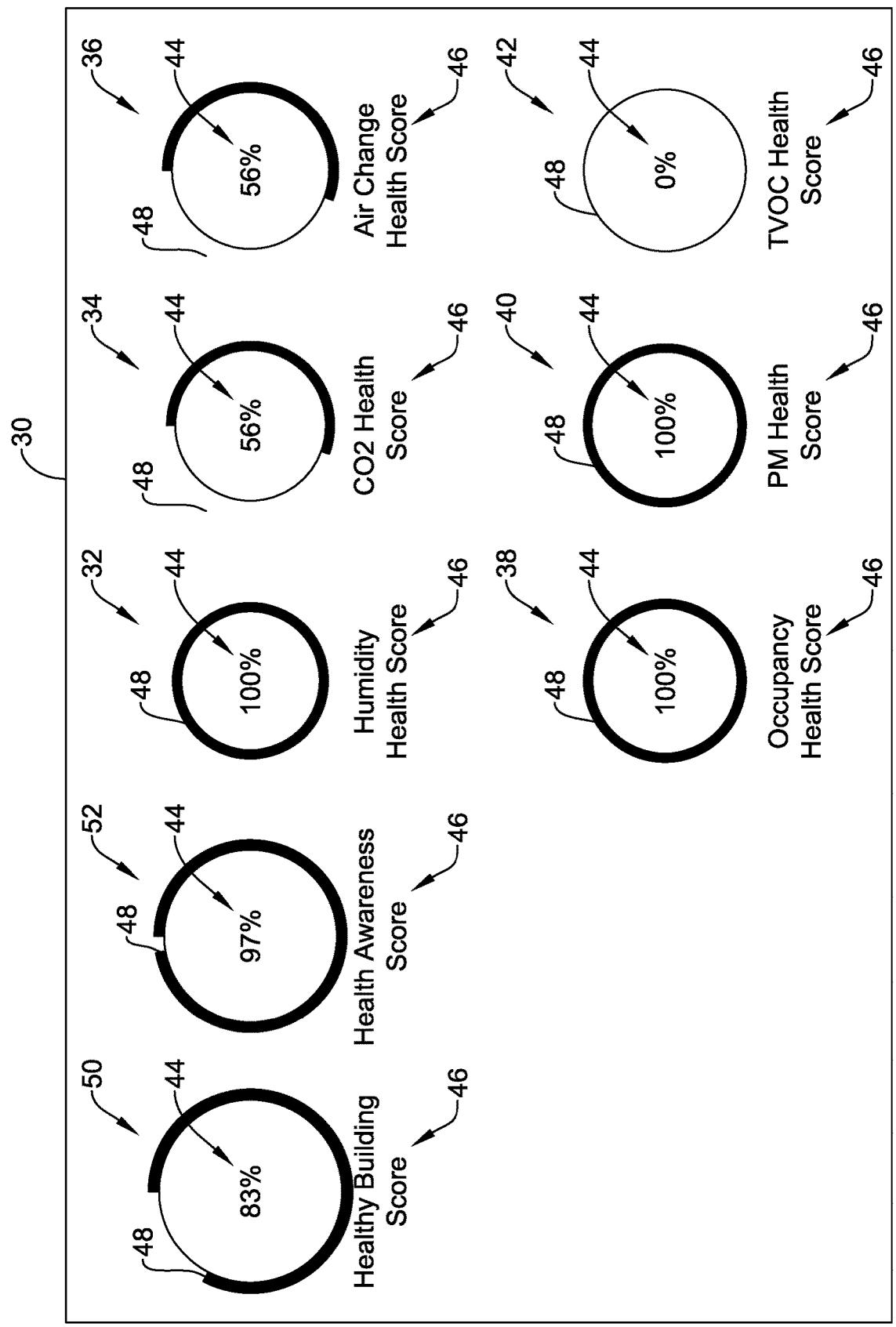
FIG. 3 is a schematic diagram of an illustrative display indicative of environmental compliance of a facility with infectious disease guidance.
Figure 5:
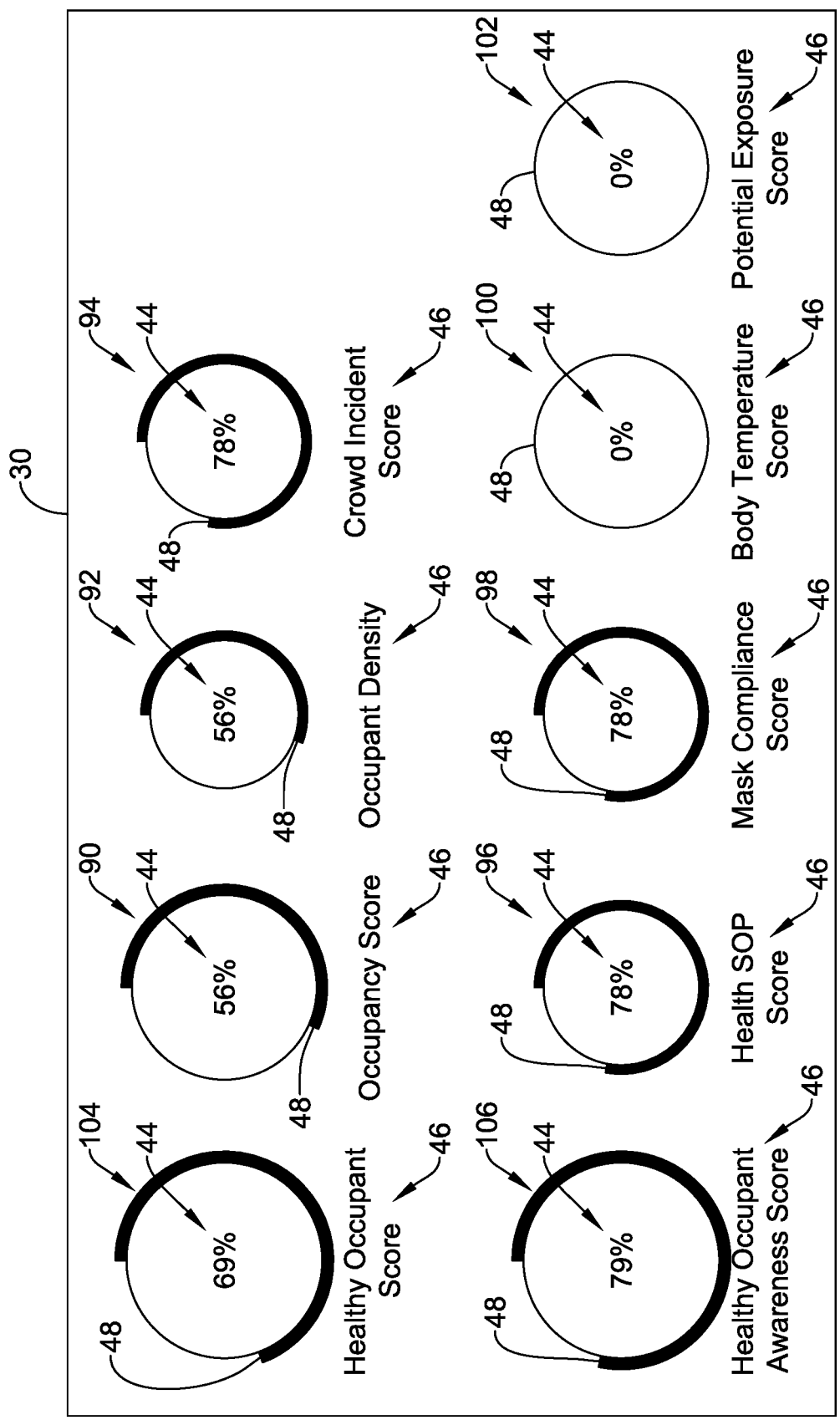
FIG. 5 is a schematic diagram of an illustrative display indicative of occupancy compliance in a facility with infectious disease guidance.

One or more of the individual scores for the determined compliance parameters associated with infectious disease guidance and/or recommendations and the overall score of the facility may be displayed 210 in a dashboard on a display (e.g., the display 26 and/or other suitable displays). Overall scores for a facility may assess, among other compliance, one or more facilities' compliance with operational best practices for controlling airborne disease transmissions, the compliance of occupants of one or more facilities with occupant best practices for controlling airborne disease transmissions, and/or compliance with other suitable infectious disease guidelines and/or recommendations. FIGS. 3 and 5 depict example dashboards displaying one or more overall scores for a facility and one or more individual scores.

In some cases, the individual scores and/or the overall scores of the facility may be utilized in a closed-loop control or in a partially closed-loop control of one or more components of building automation systems and/or to adjust operating parameters. In one example, if a $CO_2$ measurement is higher than recommended guidance in a zone of the facility, the system may adjust (e.g., via an automatic/automated control signal and/or a manually initiated control signal) the number of air exchanges per hour in that zone of the facility to reduce the $CO_2$ to a level that is within guidance. In another example, if a relative humidity level is lower than recommended guidance in a zone of the facility, the system may adjust (e.g., via an automatic/automated control signal and/or a manually initiated control signal) the relatively humidity level in that zone of the facility to increase the relative humidity to a level that is within guidance. These are just a few examples.

FIG. 3 depicts an example dashboard 30 displaying compliance of a facility with operational best practices for controlling or mitigating airborne disease transmissions. The operational best practices for controlling or mitigating airborne disease transmissions relate to compliance parameters including, but not limited to, relative humidity 32 having an individual health score of 100%, $CO_2$ 34 having an individual health score of 56%, air change 36 having an individual health score of 56%, occupancy 38 having an individual health score of 100%, particulate matter (PM) 40 having an individual health score of 100%, and TVOC 42 having an individual health score of 0%. The facility overall health score 50 is depicted in FIG. 3 as being 83%. In this case, the facility is not equipped with sensors that are suitable to measure TVOC 42, thus giving the TVOC Health Score a value of zero. This may encourage the facility manager to install one or more sensing devices that can sense TVOC to increase the Health Awareness Score 52 and/or the Health Building Score 50.

The overall health awareness score 52 is depicted in FIG. 3 as being 97%, but the overall health awareness score 52 may be omitted in some cases. The overall health awareness score 52 may be indicative of how well outfitted a facility is to comply with infectious disease guidance and/or recommendations and/or how well prepared the facility is to assess its compliance with infectious disease guidance and/or recommendations.

The individual scores for compliance parameters and/or the one or more facility scores may be displayed on the dashboard 30 in any suitable manner. The dashboard 30 may be configured to present a facility's compliance, compliance of occupants of a facility, and/or other suitable compliance with infectious disease guidance and/or recommends in a manner that is easily understandable to a facility manager and that indicates in what areas there may or may not be a need for improvement. For example, as depicted in FIG. 3, each individual score and each overall score may be provided with a numerical value 44, a name 46, and a level indicator representative of the numerical value 44 (e.g., a highlight along a circle, as in FIG. 3, a bar between a minimum value and a maximum value, etc.) for individual scores and/or the overall scores. In the example of FIG. 3, although the TVOC health score 42 is indicated as zero (0), it may be important for this individual score to be depicted so that a facility manager may easily recognize the facility does not have adequate sensing devices sensing measures from which TVOC values can be determined and/or that the values associated with TVOC are failing to comply with guidelines and/or recommendations. However, the facility manager may also view the health awareness overall score 52 and determine that it may not be worth the expense to monitor TVOC and/or improve operations relative to TVOC guidelines as the health awareness score is high (e.g., 97%) and funds may be better spent improving the $CO_2$ health score 34 and/or the air change health score 36.

The dashboard 30 may be configured in additional or alternative manners to facility users viewing, retaining, and acting-on information presented. In some cases, the various individual scores and overall scores may have different size indicators 48 (e.g., different diameter circles, as in FIG. 3 with the overall scores having a greater diameter than the individual scores, different width bars, etc.), the various individual scores and overall scores may be color-coded, buttons and/or commands may be presented for taking one or more actions and/or viewing additional data, an individual score and/or overall score may be selected for additional information (e.g., details related to a selected score including, but not limited to raw data, trend data, and/or other suitable information related to the selected score), etc.

FIG. 4 depicts an illustrative chart 60 with example information and data for the dashboard 30 depicted in FIG. 3. Although the example information and data for the dashboard 30 is depicted in a chart format in FIG. 4, other suitable data organization and/or storage techniques may be utilized.

Column 62 of the chart 60 depicts various compliance parameters used in calculating a facility's overall compliance with infectious disease guidelines and/or recommendations, along with a question as to whether the facility has a sensor or a capability to monitor and/or measure conditions related to the compliance parameters. The compliance parameters depicted in the example of FIG. 4 include percent relative humidity ("RH Percent"), carbon dioxide in parts per million ("CO2 PPM"), air exchanges per hour ("Air Changes Per Hour"), percent occupancy relative to a maximum occupancy ("Occupancy Percent"), amount of particulate matter ("PM2.5"), and amount of TVOC ("TVOC (mg/m3)").

Column 64 depicted in FIG. 4 provides raw values for each compliance parameter and may be determined (e.g., in step 204 in the method 200) from sensed and/or received values from the sensing devices 16. In column 66, an unweighted score for each raw value may be provided. As discussed above, the unweighted score for each raw value may be based on the raw value relative to one or values or ranges in the infectious disease guidelines and/or recommendations and is on a nine (9) point scale. In column 68, a weight may be provided for each compliance parameter, as well as for whether a suitable sensing device 16 is present in the facility to measure and/or monitor the compliance parameter, and is on a nine (9) point scale. Column 70 may provide a weighted metric score for a compliance parameter (e.g., "RH Percent") that may be obtained by multiplying a value in a row of column 66 with a value in the same row of column 68. Column 72 may provide a maximum possible weighted metric score and may be obtained by multiplying the weight in column 68 by a maximum possible unweighted score (e.g., nine (9) on a nine (9) point scale). Although the unweighted score in column 66 and/or the weighted metric score in column 70 may be considered an individual score for a compliance parameter, column 78 provides an individual score in percentage form that may be determined by dividing the weighted metric score in column 70 by the max possible metric score in column 72.

Column 74 may provide a weighted individual awareness score based on whether a facility has capabilities for monitoring and/or addressing a compliance parameter that may be obtained by multiplying a value in a row (e.g., "RH Sensor present?") of column 66 with a value in the same row of column 68. Column 76 may provide a maximum possible weighted awareness score and may be obtained by multiply the weight in column 68 by a maximum possible unweighted score (e.g., nine (9) on a nine (9) point scale).

In row 80, the values in column 70, column 72, column 74, and column 76 may be summed to provide total values for a facility. From the total values for a facility in the row 80, a percent compliance with infectious disease guidelines and/or recommendations 84 and a percent awareness of infectious disease guidelines and/or recommendations 86 may be provided in row 82. The percent compliance with infectious disease guidelines and/or recommendations 84 may be determined by dividing the total weighted metric score from column 70, row 80 by the maximum possible metric score from column 72, row 80. The awareness score of infectious disease guidelines and/or recommendations 86 may be determined by dividing the total weighted awareness score from column 74, row 80 by the maximum possible awareness score from column 78, row 80. Further, in box 88, the percent compliance with infectious disease guidelines and/or recommendations 84 may be provided as the Facility Health Score and the awareness score of infectious disease guidelines and/or recommendations 86 may be provided as the Facility Health Awareness score.

FIG. 5 depicts an example dashboard 30 displaying compliance metrics of occupants in a facility with a set of occupant best practices for mitigating airborne disease transmissions. The occupant best practices for mitigating airborne disease transmissions relate to compliance parameters including, but not limited to, occupancy 90 having an individual score of 56%, occupancy density 92 having an individual score of 56%, crowd incident 94 having an individual score of 78%, a health standard operating procedure (SOP) compliance 96 having an individual score of 78%, a mask compliance 98 individual score of 78%, a body temperature incident 100 having an individual score of 0%, and a potential individual exposure 102 having an individual score of 0%. The facility occupant health score 104 is depicted in FIG. 5 as being 69%.

Additionally, a facility occupant awareness score 106 is depicted in FIG. 5 as being 79%, but the facility occupant awareness score 106 may be omitted. The facility occupant awareness score 106 may be indicative of how well prepared a facility is to facilitate occupants' compliance with infectious disease guidance and/or recommendations and/or how well prepared the facility is to assess occupants' compliance with infectious disease guidance and/or recommendations.

Similar to as discussed above with respect to FIG. 3, the individual scores for compliance parameters related to guidelines and/or recommendations for facility occupants/occupancy and/or the one or more overall facility occupant scores may be displayed on the dashboard 30 of FIG. 5 in any suitable manner. In one example, as depicted in FIG. 5, each individual score and each overall score may be provided with the numerical value 44, a name 46, and a level indicator 48 (e.g., a highlight along a circle, as in FIG. 3, a bar between a minimum value and a maximum value, etc.) representative of the numerical value 44 for individual scores and/or the overall scores.

In the example of FIG. 5, although the body temperature individual score 100 and the potential exposure individual score 102 are indicated as being zero (0), it may be important for these individual scores to be depicted so that a facility manager may easily recognize the facility does not have adequate sensing devices for sensing measures from which body temperature values and potential exposure values can be determined and/or that the values associated with monitoring body temperature and potential exposure to an infectious disease are failing to comply with guidelines and/or recommendations. However, the facility manager may also view the health occupant awareness overall score 106 and determine that it may or may not be worth the expense to monitor body temperature and potential exposure and/or improve operations relative to body temperature and potential exposure guidelines as the health awareness score may be relatively high (e.g., 79%) and funds may be better spent improving the occupancy score 90, the occupant density score 92, which are relative low (e.g., both are at 56% in FIG. 5), and/or other scores.

The dashboard 30 may be configured in additional or alternative manners to facilitate users viewing, retaining, and/or acting-on information presented. In some cases, the various individual scores and overall scores may have different size indicators 48 (e.g., different diameter circles, as in FIG. 5 with respect to the overall scores relative to individual scores, different width bars, etc.), the various individual scores and overall scores may be color-coded, buttons and/or commands may be presented for taking one or more actions and/or viewing additional data, an individual score, overall score may be selected for additional information (e.g., details related to a selected score including, but not limited to raw data, trend data, and/or other suitable information related to the selected score), etc.

FIG. 6 depicts an illustrative chart 110 with example information and data for the dashboard depicted in FIG. 5. Although example information and data for the dashboard is depicted in a chart format in FIG. 5, other suitable data organization and/or storage techniques may be utilized.

Column 112 of the chart 110 may depict various compliance parameters used in calculating an overall compliance of facility occupants with infectious disease guidelines and/or recommendations, along with a question as to whether the facility has a sensor or a capability to monitor and/or measure conditions related to the compliance parameters. The compliance parameters depicted in FIG. 6 include percent occupancy relative to a maximum occupancy ("Occupancy Level (%)"), occupancy density in people per square foot ("Density (people per sq ft"), identified crowds per day ("Crowd Incidents per day (8 or more people)"), compliance with health related standard operating procedures ("Health Compliance SOP Closed (%)"), percent of occupants wearing a mask ("Mask Compliance"), incidents of identified elevated body temperature ("Elevated Body Temperature Incidents (%)"), and an amount of people potentially exposed to an infectious disease ("People Potentially Exposed (via contact traces)"). Other potential compliance parameters are contemplated.

Column 114 depicted in FIG. 6 may provide raw values for each compliance parameter and may be determined (e.g., in step 204 in the method 200) from sensed and/or received values from the sensing devices 16. In column 116, an unweighted score for each raw value may be provided. As discussed above, the unweighted score for each raw value may be based on the raw value relative to one or values or ranges in the infectious disease guidelines and/or recommendations and, in the example of FIGS. 5 and 6, is on a nine (9) point scale, but other scales are contemplated. In column 118, a weight may be provided for each compliance parameter, as well as for whether a suitable sensing device 16 is present the facility to measure and/or monitor the compliance parameter, and, in the example of FIGS. 5 and 6, is on a nine (9) point scale, but other scales are contemplated. Column 120 provides a weighted metric score for a compliance parameter (e.g., "Occupancy Level (%)") that may be obtained by multiplying a value in a row of column 116 with a value in the same row of column 118. Column 122 provides a maximum possible weighted metric score and may be obtained by multiplying the weight in column 118 by a maximum possible unweighted score (e.g., nine (9) on a nine (9) point scale). Although the unweighted score in column 116 and/or the weighted metric score in column 120 may be considered an individual score for a compliance parameter, column 128 may provide an individual score in percentage form that may be determined by dividing the weighted metric score in column 120 by the maximum possible weighted metric score in column 122.

Column 124 may provide a weighted individual awareness score based on whether a facility has capabilities for monitoring and/or addressing a compliance parameter that may be obtained by multiplying a value in a row (e.g., "Occupancy available?") of column 116 with a value in the same row of column 118. Column 126 may provide a maximum possible weighted awareness score and may be obtained by multiply the weight in column 118 by a maximum possible unweighted score (e.g., nine (9) on a nine (9) point scale).

In row 130, the values in column 120, column 122, column 124, and column 126 may be summed to provide total values for facility occupants. From the total values for facility occupants in the row 130, a percent compliance 134 with infectious disease guidelines and/or recommendations for occupants of a facility and a percent awareness 136 of infectious disease guidelines and/or recommendations for occupants of a facility may be provided in row 132. The percent compliance 134 with infectious disease guidelines and/or recommendations may be determined by dividing the total weighted metric score from column 120, row 130 by the maximum possible metric score from column 122, row 130. The awareness score 136 of infectious disease guidelines and/or recommendations may be determined by dividing the total weighted awareness score from column 124, row 130 by the maximum possible awareness score from column 128, row 130. Further, in box 138, the percent compliance 134 with infectious disease guidelines and/or recommendations may be provided as the Health Occupant Score (e.g., 104 in FIG. 5) and the awareness score 136 of infectious disease guidelines and/or recommendations may be provide as the Health Occupant Awareness Score (e.g., 106 in FIG. 5).

When various scores for facilities are determined for a plurality of various guidelines and/or recommendations, it is contemplated that a score for a facility and/or a score for a compliance parameter relative to a first guideline and/or recommendation may affect a value of a weight and/or a score of a compliance parameter taken into account in a score for a facility relative to one or more other guidelines and/or recommendations. For example, a greater occupancy level (e.g., a higher occupancy percent relative to a maximum occupancy) may be allowed (e.g., scored higher) when scoring facility occupants relative to infectious disease guidelines and/or recommendations (e.g., as in FIGS. 5 and 6) if a humidity level being scored for determining a facility's compliance with infectious disease guidelines and/or recommendations (e.g., as in FIGS. 3 and 4) is within a preferred range. Other examples are contemplated.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. In the foregoing Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

What is claimed is:

1. A method for assessing compliance with infectious disease guidance for reducing airborne disease transmission in a facility, the infectious disease guidance including a plurality of recommendations that can be assessed by a plurality of sensing devices, the method comprising:
sensing a plurality of conditions in the facility using the plurality of sensing devices;
determining a compliance parameter for each of two or more of the plurality of recommendations of the infectious disease guidance based at least in part on one or more of the plurality of sensed conditions, wherein the plurality of recommendations of the infectious disease guidance include recommendations related to one or more of relative humidity in the facility, $CO_2$ concentration in the facility, air change rates in the facility, occupancy in the facility, particulate matter concentrations in the facility, and Total Volatile Organic Compound (TVOC) concentrations in the facility;

determining an individual score for each of the determined compliance parameters, wherein each of the individual scores provide a measure of how well the corresponding compliance parameter is considered to satisfy the corresponding recommendation of the infectious disease guidance;

determining an overall score of the facility by aggregating the individual scores associated with each of the two or more of the plurality of recommendations of the infectious disease guidance; and displaying a dashboard on a display that concurrently displays the overall score of the facility as well as one or more of the individual scores.

2. The method of claim 1, wherein aggregating the individual scores associated with each of the two or more of the plurality of recommendations of the infectious disease guidance comprises assigning a weight to each of the individual scores and then aggregating the individual scores based at least in part on their assigned weights.

3. The method of claim 1, wherein each of the individual scores are scaled to be between 0% and 100%.

4. The method of claim 1, wherein when the facility does not currently have a sensing device that can sense a condition from which a corresponding compliance parameter can be determined for one or more of the plurality of recommendations of the infectious disease guidance, the method comprising assigning an individual score of zero to the compliance parameter that cannot be determined.

5. The method of claim 4, further comprising displaying on the dashboard the individual scores that correspond to the compliance parameter that cannot be determined to encourage an installation of one or more sensing devices that can sense a condition from which the compliance parameters that could not be determined can be determined.

6. The method of claim 5, further comprising:
determining a health awareness score that provides a measure of how well the facility is equipped with sensing devices to determine compliance parameters for each of the plurality of recommendations of the infectious disease guidance that can be assessed by one or more sensing devices; and
displaying the health awareness score on the dashboard.

7. The method of claim 1, wherein:
one of the plurality of recommendations of the infectious disease guidance includes a recommendation that the relative humidity inside of the facility be within a recommended relative humidity range;
wherein a sensed condition comprises relative humidity in the facility, and wherein the compliance parameter comprises a current sensed relative humidity value; and
the individual score for the current sensed relative humidity value is determined based on how well the current sensed relative humidity value meets the recommended relative humidity range.

8. The method of claim 1, wherein:
one of the plurality of recommendations of the infectious disease guidance includes a maximum occupancy level in the facility;
wherein a sensed condition comprises an occupant detection in the facility, and wherein the compliance parameter comprises a current occupant count in the facility; and the individual score for the current occupant count in the facility is determined based on comparing the current occupant count with the maximum occupancy level of the recommendation.

9. The method of claim 1, wherein the plurality of recommendations of the infectious disease guidance include recommendations related to one or more of maximum occupancy level in the facility, maximum occupancy density in the facility, number of crowd incidence per day, percent of health related standard operating procedure actions closed, mask compliance in the facility, elevated body temperature incidents, and number of people potentially exposed to an individual infected with infectious disease via contact tracing.

10. The method of claim 1, wherein the one of the plurality of sensing devices comprises an air sensor.

11. The method of claim 1, wherein the one of the plurality of sensing devices comprises a control signal monitor.

12. The method of claim 1, wherein the one of the plurality of sensing devices comprises a video camera.

13. The method of claim 1, wherein the one of the plurality of sensing devices comprises an occupancy sensor.

14. A non-transitory computer readable medium storing instructions that when executed by a processor cause the processor to:
receive a plurality of sensed conditions in a facility sensed by a plurality of sensing devices;
determine a compliance parameter for each of at least two recommendations of an infectious disease guidance based at least in part on one or more of the plurality of sensed conditions;
determine an individual score for each of the determined compliance parameters, wherein each of the individual scores provide a measure of how well the corresponding compliance parameter is considered to satisfy the corresponding recommendation of the infectious disease guidance; and
display on a display one or more of the individual scores.

15. The non-transitory computer readable medium of claim 14, wherein the instructions cause the processor to:
determine an overall score of the facility by aggregating the individual scores associated with each of the at least two recommendations of the infectious disease guidance; and
display on the display the overall score.

16. The non-transitory computer readable medium of claim 15, wherein aggregating the individual scores associated with each of the at least two recommendations of the infectious disease guidance comprises assigning a weight to each of the individual scores and then aggregating the individual scores based at least in part on their assigned weights.

17. The non-transitory non transient computer readable medium of claim 15, wherein each of the individual scores are scaled to be between 0% and 100%.

18. A system for assessing compliance with infectious disease guidance for reducing airborne disease transmission in a facility, the infectious disease guidance including a plurality of recommendations that can be assessed by one or more sensing devices, the system comprising:
a memory for storing a plurality of conditions in the facility sensed by a plurality of sensing devices;
a controller operatively coupled to the memory, the controller configured to:
determine a compliance parameter for two or more of the plurality of recommendations of the infectious disease guidance based at least in part on one or more of the plurality of sensed conditions;

determine an individual score for each of the determined compliance parameters, wherein each of the individual scores provide a measure of how well the corresponding compliance parameter is considered to satisfy the corresponding recommendation of the infectious disease guidance;

assign an individual score of zero to a compliance parameter for one or more of the plurality of recommendations of the infectious disease guidance that cannot be determined because the memory does not currently store a condition from which the corresponding compliance parameter can be determined;

display on a display the one or more of the individual scores including one or more of the individual scores that correspond to the compliance parameters that cannot be determined to encourage an installation of one or more sensing devices that can sense a condition from which the compliance parameters that could not be determined can be determined.

19. The system of claim 18, wherein the controller is configured to:

determine an overall score of the facility by aggregating the individual scores associated with each of the plurality of recommendations; and display on the display the overall score concurrently with one or more of the one or more of the individual scores.

\* \* \* \* \*